US007729749B2

(12) United States Patent
Roessler et al.

(10) Patent No.: US 7,729,749 B2
(45) Date of Patent: Jun. 1, 2010

(54) METHOD AND APPARATUS FOR EVALUATING CONNECTIVE TISSUE CONDITIONS

(75) Inventors: Blake J. Roessler, Ann Arbor, MI (US); Michael D. Morris, Ann Arbor, MI (US); Karen A. Dehring, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 389 days.

(21) Appl. No.: 11/217,755

(22) Filed: Sep. 1, 2005

(65) Prior Publication Data

US 2007/0049808 A1 Mar. 1, 2007

(51) Int. Cl.
*A61B 6/00* (2006.01)
(52) U.S. Cl. .................... 600/476; 356/301
(58) Field of Classification Search ........ 600/407, 600/473, 475–477; 250/339.07, 339.08; 356/451–456, 72–73, 301; 436/63–64
See application file for complete search history.

(56) References Cited

U.S. PATENT DOCUMENTS

| 4,321,930 | A | 3/1982 | Jobsis et al. |
|---|---|---|---|
| 4,635,643 | A | 1/1987 | Brown |
| 4,986,273 | A | 1/1991 | O'Neill et al. |
| 5,139,025 | A | 8/1992 | Lewis et al. |
| 5,197,470 | A | 3/1993 | Helfer et al. |
| 5,293,872 | A | 3/1994 | Alfano et al. |
| 5,452,723 | A | 9/1995 | Wu et al. |
| 5,615,673 | A | 4/1997 | Berger et al. |
| 5,987,346 | A | 11/1999 | Benaron et al. |
| 5,991,653 | A | 11/1999 | Richards-Kortum et al. |
| 6,040,906 | A | 3/2000 | Harhay |
| 6,060,169 | A | 5/2000 | Kuczynski et al. |
| 6,070,583 | A | 6/2000 | Perelman et al. |

(Continued)

FOREIGN PATENT DOCUMENTS

EP 0 761 161 3/1997

(Continued)

OTHER PUBLICATIONS

Adamson, *Physical Chemistry of Surfaces*, pp. 496-497, (4th Ed. John Wiley and Sons, New York, 1982).

(Continued)

*Primary Examiner*—Brian Casler
*Assistant Examiner*—Jonathan G Cwern
(74) *Attorney, Agent, or Firm*—Marshall, Gerstein & Borun LLP

(57) ABSTRACT

Methods and apparatus are provided for evaluating a connective tissue condition of a patient (e.g., a disease, a risk of developing a disease, a risk of developing a fracture, etc.). For example, an indicator associated with the connective tissue condition may be generated. First, tissue at a first location of the body of the patient is irradiated using a light source. The tissue may be irradiated in vivo through the skin or via an incision, for example. Alternatively, a biopsy of the tissue may be irradiated. Then, spectral content information for light scattered, reflected, or transmitted by the irradiated tissue is determined. The spectral content information may be used, at least in part, to generate an indicator associated with a condition of connective tissue at a second location of the body of the patient, the second location remote from the first location. The indicator may, for example, assist a physician in diagnosing or ruling out the connective tissue condition.

32 Claims, 12 Drawing Sheets

U.S. PATENT DOCUMENTS

| | | | |
|---|---|---|---|
| 6,072,180 | A | 6/2000 | Kramer et al. |
| 6,196,226 | B1 | 3/2001 | Hochman et al. |
| 6,213,958 | B1 | 4/2001 | Winder |
| 6,285,901 | B1 | 9/2001 | Taicher et al. |
| 6,353,753 | B1 | 3/2002 | Flock et al. |
| 6,370,422 | B1 | 4/2002 | Richards-Kortum et al. |
| 6,373,567 | B1 | 4/2002 | Wise et al. |
| 6,385,484 | B2 | 5/2002 | Nordstrom et al. |
| 6,445,767 | B1 | 9/2002 | Karellas |
| 6,490,339 | B2 | 12/2002 | Mitchell et al. |
| 6,574,490 | B2* | 6/2003 | Abbink et al. ............... 600/316 |
| 6,690,966 | B1 | 2/2004 | Rava et al. |
| 6,697,665 | B1 | 2/2004 | Rava et al. |
| 6,949,635 | B1 | 9/2005 | Kumar et al. |
| 2002/0002336 | A1 | 1/2002 | Marchitto et al. |
| 2002/0010400 | A1* | 1/2002 | Camacho et al. ............ 600/473 |
| 2002/0150938 | A1 | 10/2002 | Kneipp et al. |
| 2002/0156380 | A1 | 10/2002 | Feld et al. |
| 2002/0169379 | A1 | 11/2002 | Camacho et al. |
| 2003/0130579 | A1* | 7/2003 | McClane et al. ............ 600/476 |
| 2003/0191398 | A1 | 10/2003 | Motz et al. |
| 2004/0073120 | A1 | 4/2004 | Motz et al. |
| 2004/0186383 | A1 | 9/2004 | Rava et al. |
| 2005/0003376 | A1 | 1/2005 | Kneipp et al. |
| 2005/0031181 | A1* | 2/2005 | Bi et al. ...................... 382/132 |
| 2005/0261568 | A1 | 11/2005 | Hular et al. |
| 2008/0076985 | A1 | 3/2008 | Matousek et al. |
| 2008/0129992 | A1 | 6/2008 | Matousek et al. |

FOREIGN PATENT DOCUMENTS

| | | |
|---|---|---|
| WO | WO 01/52739 | 7/2001 |
| WO | WO 02/03857 | 1/2002 |
| WO | WO-2005/004714 A1 | 1/2005 |
| WO | WO-2006/061565 A1 | 6/2006 |
| WO | WO-2006/061566 A1 | 6/2006 |

OTHER PUBLICATIONS

Akkus et al., "Aging of microstructural compartments in human compact bone," *J. Bone Miner. Res.* 18:1012-1019 (2003).

Akkus et al., "Age-related changes in physiochemical properties of mineral crystals are related to impaired mechanical function of cortical bone," *Bone* 34: 443-453, 2004.

Bakker et al., "In Vivo Detection of Dysplastic Tissue by Raman Spectroscopy," *Analytical Chemistry*, 72(24): 6010-6018 (2000).

Bandekar, "Amide Modes and Protein Conformation," *Biochimica et Biophysica Acta* 1120:123-143 (1992).

Bentolila et al., "Intracortical remodeling in adult rat long bones after fatigue loading," *Bone* 23:275-281(1998).

Bihan et al., "Determination of the Secondary Structure and Conformation of Puroindolines by Infrared and Raman Spectroscopy," *Biochemistry* 35: 12712-12722 (1996).

Bloebaum et al., "Determining mineral content variations in bone using backscattered electron imaging," *Bone* 20:485-590 (1997).

Bohic et al., "Characterization of the Trabecular Rat Bone Mineral: Effect of Ovariectomy and Bisphosphonate Treatment," *Bone.* 26(4): 341-348 (2000).

Boivin et al., "Strontium Distribution and Interactions with Bone Mineral in Monkey Lliac Bone after Strontium Salt (S 12911) Administration," *Journal of Bone & Mineral Research*, 11(9): 1302-11 (1996).

Boyce et al, "Cortical aging differences and fracture implications for the human femoral neck," *Bone* 14:769-78 (1993).

Boyde et al., "Mineral density quantitation of the human cortical iliac crest by backscattered electron image analysis: variations with age, sex, and degree of osteoarthritis," *Bone* 16:619-27 (1995).

Boyde et al., "Effect of estrogen suppresion on the mineralization density of iliac crest biopsies in young women as assessed by backscattered electron imaging," *Bone* 22:241-50 (1998).

Buchanan, "Assessment of the risk of vertebial fracture in menopausal women," *J. Bone & Joint Surg.* 69:212-218 (1987).

Burr et al., "Alterations to the en bloc basic fuchsin staining protocol for the demonstration of microdamage produced in vivo," *Bone* 17:431-433 (1995).

Burr, "Microdamage and bone fragility," *Current Opinion in Orthopaedics* 12:365-370, 2001.

Burr et al., "Bone Microdamage and Skeletal Fragility in Osteoporotic and Stress Fractures," *J. Bone and Mineral. Res.* vol. 12, No. 1:6-15 (1997).

Bussian, "How To Determine Protein Secondary Structure in Solution by Raman Spectroscopy: Practical Guide and Test Case DNase I," *Biochemistry* 28:4271-4277 (1989).

Carden et al., "Raman Imaging of Bone Mineral and Matrix: Composition and Function," *Proc. S.P.I.E.*, vol. 3608:132-138 (1999).

Carden et al., "Ultrastructural Changes Accompanying the Mechanical Deformation of Bone Tissue: A Raman Imaging Study," *Calcif. Tissue Int.*, vol. 72;166-175 (published online Dec. 2002).

Carden et al., "Application of vibrational spectroscopy to the study of mineralized tissues," *J. Biomedical Optics*, vol. 5, No. 3:259-268 (2000).

Chirgadze et al., "Infrared Spectra and Resonance Interaction of Amide I Vibration of the Antiparallel-Chain Pleated Sheet," *Biopolymers* 15:607-625 (1976).

Chirgadze et al., "Infrared Spectra and Resonance Interaction of Amide I Vibration of the Parallel-Chain Pleated Sheet," *Biopolymers* 15:627-636 (1976).

Choi et al., "A comparison of the fatigue behavior of human trabecular and cortical bone tissue," *J. Biomech.* 25:1371-1381 (1992).

Choi et al., "The elastic moduli of human subchondral, trabecular, and cortical bone tissue and the size-dependency of cortical bone modulus," *J. Biomech.*23:1103-1113 (1990).

Ciarelli et al., "Architectural and material contributions to fracture of the spine and proximal femur," Doctoral Dissertation, University of Michigan (1998).

Ciarelli et al., "Variations in Three-Dimensional Cancellous Bone Architecture of the Proximal Femur in Female Hip Fractures and in Controls," *J. Bone and Mineral Res.* vol. 15, No. 1:166-175 (2000).

Cody et al., "Femoral Strength is Better Predicted by Finite Element Models than QCT and DXA," *Journal of Biomechanics*, vol. 32, No. 10:1013-1020 (1999).

Crane et al. "Spectral imaging of mouse skulls undergoing craniosynstosis," *Proc. SPIE* 4959:111-119 (2003).

Crofts et al., "Aging changes in osteon mineralization in the human femoral neck," *Bone* 15:147-52 (1994).

Cummings, S.R., "Are Patients with Hip Fractures More Osteoporotic?" *American Journal of Medicine* 78:487-494, Mar. 1985.

Currey, "The effect of porosity and mineral content on the Young's modulus of elasticity of compact bone," *J. Biomech.* 21:131-139 (1988).

Das et al., "Time-resolved fluorescence and photon migration studies in biomedical and model random media," *Rep. Prog. Physics* vol. 60:227-292 (1997).

Frushour et al., "Raman spectroscopic study of mechanically deformed poly-L-alanine," *Biopolymers* 13:455-474 (1974).

Garfinkel et al., "Raman spectra of amino acids and related compounds," *Am. Chem. Soc.* 80:3818 (1958).

Grynpas et al., "Subchondral bone in osteoarthritis," *Calcif. Tissue Int.* 49:20-26 (1991).

Grynpas, "Age and disease-related changes in the mineral of bone," *Calcif. Tissue Int.* 53:S57-S64 (1993).

Hoffler et al., "Age, gender, and bone lamellae elastic moduli," *J. Orthop. Res.* 18:432-437 (2000).

Ichimura et al., "Local enhancement of coherent anti-Stokes Raman scattering by isolated gold nanoparticles," *J. Raman Spectroscopy* 34:651-654 (2003).

Jordan et al., "Spatial clustering of remodeling osteons in the femoral neck cortex: A cause of weakness in hip fracture?" *Bone* 26:305-313 (2000).

Kaminaka et al., "Near-infrared multichannel Raman spectroscopy toward real-time in vivo cancer diagnosis," *J. Raman Spectroscopy*, vol. 33, issue 7:498-502 (Jul. 10, 2002).

Katz et al., "Qualitative Bone Mineral Changes in Osteoporosis," 33rd Annual Meeting of the Orthopaedic Research Society, San Francisco, CA, p. 263 (1987).

Kingsmill, "Mineralisation density of human mandibular bone: quantitative backscattered electron image analysis," *J. Anat.* 192:245-256 (1998).

Kuhn et al., "Comparison of the trabecular and cortical tissue moduli from human iliac crests," *J. Orthop. Res.* 7:876-884 (1989).

Lakshmi et al., "Osteoradionecrosis (ORN) of the mandible: A laser Raman spectroscopic study," *Appl. Spectroscopy* 57:1100-1116 (2003).

Lewis et al., "Fiber-optic Probes for Raman Spectrometry," in *Handbook of Vibrational Spectroscopy*, vol. 2, pp. 1587-1597 (John M. Chalmers & Peter R. Griffiths eds. 2002).

McCreadie et al., "Perspective: Biomechanics of Fracture:Is Bone Mineral Density Sufficient to Assess Risk?" *Journal of Bone and Mineral Research*, vol. 15, No. 12:. 2305-2308 (2000).

Mendelsohn et al., "IR Microscopic Imaging of Pathological States and Fracture Healing of Bone," *Applied Spectroscopy* vol. 54, No. 8: 1183-1191 (2000).

Mente et al., "Experimental method for the measurement of the elastic modulus of trabecular bone tissue," *J. Orthop. Res.* 7:456-461 (1989).

Miller et al., "Synchrotron Infrared Microspectroscopy: A New Techique for Probing the Chemical Composition of Bone and its Implications for Understanding Osteoarthritis," *National Synchrotron Light Source, 1997 Activity Report*, pp. 2-34 to 2-35, (1997), available at http://www.nsls.bnl.gov/newsroom/publications/activityreport/1997/2instrum.pdf.

Morris et al., "Bone microstructure deformation observed by Raman microscopy," *Proc SPIE* 4254:81-89 (2001).

Morris et al., "Effects of Applied Load on Bone Tissue as Observed by Raman Spectroscopy," *Proc SPIE* 4614:47-54 (2002).

Morris et al., "Raman microscopy of de novo woven bone tissue," *Proc. SPIE* 4254:90-96 (2001).

Nabiev et al., "Selective Analysis of Antitumor Drug Interaction with Living Cancer Cells is Probed by Surface-Enhanced Raman Spectroscopy," *Eur. Biophysics J.* 19(6):311-316 (1991).

Otsu, "A threshold selection method from gray-level histograms," *IEEE Trans. on Systems, Man and Cybernetics* SMC-9:62-66 (1979).

Otto, *Chemometrics: Statistics and Computer Application in Analytical Chemistry*, pp. 28-39 (1999).

Paschalis et al., "FTIR Microspectroscopic Analysis of Human Iliac Crest Biopsies from Untreated Osteoporotic Bone," *Calcified Tissue International*, 61(6):487-492 (1997).

Paschalis et al., "FTIR Microspectroscopic Analysis of Human Osteonal Bone," *Calcif. Tissue Int.* vol. 59:480-487 (1996).

Pelton et al., "Spectroscopic Methods for Analysis of Protein Secondary Structure," *Anal. Biochem.* 277:167-176 (2000).

Pezzuti et al., "Hyperspectral Raman Imaging of Bone Growth and Regrowth Chemistry," *S.P.I.E.* vol. 3261:270-276 (1998).

Pillay, I., "The Use of Fingernails as a Means of Assessing Bone Health: A Pilot Study," *Journal of Women's Health* 14(4), 339-344, May 2005.

Reid et al., "Changes in the mineral density distribution in human bone with age: image analysis using backscattered electrons in the SEM," *J. Bone Mineral Res.* 2:13-22 (1987).

Renugopalakrishnan et al., "Non-uniform Triple Helical Structure in Chick Skin Type I Collagen on Thermal Denaturation: Raman Spectroscopic Study," *Z. Naturforsch* [C]53:383-88 (1998).

Rey et al., "Resolution-Enhanced Fourier Transform Infared Spectroscopy Study of the Environment of Phosphate Ion in the Early Deposits of a Solid Phase of Calcium Phosphate in Bone and Enamel and their Evolution with Age: 2. Investigations in the $v_3PO_4$ Domain," *Calcif. Tissue Int.* vol. 49:383-388 (1991).

Rho et al., "Young's modulus of trabecular and cortical bone material: ultrasonic and microtensile measurements," *J. Biomech.* 26:111-119 (1993).

Riemer, "Characterization of the architecture, tissue properties, and continuum behavior of aging trabecular bone," *Orthopaedic Transactions* 18:421-422 (1994).

Riggs et al., "Differential changes in bone mineral density of the appendicular and axial skeleton with aging: Relationship to spinal osteoporosis," *J. Clin. Invest.* 67:328-335 (1981).

Riggs et al., "Changes in Bone Mineral Density of the Proximal Femur and Spine with Aging," *J. Clin. Invest.* vol. 70:716-723 (1982).

Roschger et al., "Mineralization of cancellous bone after alendronate and sodium fluoride treatment: a quantitative backscattered electron imaging study on minipig ribs," *Bone* 20:393-97 (1997).

Roschger et al., "Validation of quantitative backscattered electron imaging for the measurement of mineral density distribution in human bone biopsies," *Bone* 23:319-26 (1998).

Skedros et al., "Influence of mineral content and composition on graylevels in backscattered electron images of bone," *J. Biomed. Materials Res.* 27:57-64 (1993).

Skedros et al., "The meaning of graylevels in backscattered electron images of bone," *J. Biomed. Materials Res.* 27:47-56 (1993).

Tadrous, "Methods for Imaging the Structure and Function of Living Tissues and Cells," Oct. 12, 2002, at http://www.bialith.com/Teaching/PathologyPG/BAMScHCInV.PDF.

Tarnowski et. al., "Mineralization of Developing Mouse Calvaria as Revealed by Raman Microspectroscopy," *J. Bone Miner. Res.* 17:1-9 (2002).

Timlin et al., "Chemical microstructure of cortical bone probed by Raman transects," *Applied Spectroscopy* 53:1429-1435 (1999).

Timlin et al., "Raman Spectroscopic Imaging Markers for Fatigue-Related Microdamage in Bovine Bone," *Anal. Chem.* 72:2229-2236 (2000).

Timlin et al., "Spatial Distribution of Phosphate Species in Mature and Newly Generated Mammalian Bone by Hyperspectral Raman Imaging," *Journal of Biomedical Optics*, vol. 4, No. 1:28-34 (1999).

Torreggiani et al., "Interaction of Biotin and Biotinyl Derivatives with Avidin: Conformational Changes Upon Binding," *J. Raman Spectroscopy* 31:445-450 (2000).

Townsend et al., "Buckling studies of single human trabeculae," *J. Biomech.* 8:199-201 (1975).

Wang et al., "Determination of Molecular Changes in Soft Tissues Under Strain Using Laser Raman Microscopy," *J. Biomech.* 33:483-486 (2000).

Wentrup-Byrne et al., "Fourier transform Raman microscopic mapping of the molecular components in a human tooth," *J. Raman Spectroscopy* 28:151-158 (1997).

West et al., "Fourier Transform Infrared Spectral Analysis of Degenerative Cartilage: An Infrared Fiber Optic Probe and Imaging Study," *Applied Spectroscopy*, vol. 58, No. 4:376-381 (Apr. 2004).

Zhang et al., "Mechanisms of Growth and Dissolution of Sparingly Soluble Salts; Mineral-Water Interface Geochemistry," in *Reviews Mineralogy: Mineral-Water Interface Geochemistry*, vol. 23:368-396 (M. Hochella, Jr. and A. White eds. 1990).

"Predicting When Bones May Break," The Whitaker Foundation News, (2000) www.whitaker.org/news.

Search Results from U.S. Appl. No. 09/765,989 dated Jun. 9, 2002.

Search Results from U.S. Appl. No. 09/765,989 dated Jan. 14, 2003.

Search.Results from U.S. Appl. No. 09/765,989 dated Jan. 27, 2003.

International Search Report issued by ISA in PCT/US2004/020858 mailed Oct. 27, 2004.

International Search Report issued by ISA in PCT/US2004/044038 mailed May 25, 2005.

Written Opinion issued in PCT/US2004/044038 mailed May 25, 2005.

Awonusi, A., et al., "Carbonate Assignment and Calibration in the Raman Spectrum of Apatite," Calcif. Tissue Int., vol. 81, pp. 46-52, 2007.

McCreadie, B., et al., "Bone tissue compositional differences in women with and without osteoporotic fracture," Bone, vol. 39, pp. 1190-1195, 2006.

Mendelsohn, R., et al., "Infrared Spectroscopy, Microscopy, and Microscopic Imaging of Mineralizing Tissues: Spectra-Structure Correlations from Human Iliac Crest Biopsies,"*J. Biomedical Optics*, vol. 4, No. 1, pp. 14-21, 1999.

Rey, C., et al., "Fourier Transform Infrared Spectroscopic Study of the Carbonate Ions in Bone Mineral During Aging," Calcif. Tissue Int., vol. 49, pp. 252-258, 1991.

Shim, M., et al., "Study of Fiber-Optic Probes for in Vivo Medical Raman Spectroscopy", Applied Spectroscopy, vol. 53, No. 6, pp. 619-627, 1999.

Abstract of Boskey et al., "Fourier transform infrared microspectroscopic analysis of bones of osteocalcin-deficient mice provides insight into the function of osteocalcin," Bone, 23(3):187-196 (1998).

Behrend et al., "Identification of outliers in hyperspectral Raman image data by nearest neighbor comparison," Appl. Spectrosc., 56:1485-1488 (2002).

Carden et al., "Ultrastructural Changes Accompanying the Mechanical Deformation of Bone Tissue: A Raman Imaging Study," Calcified Tissue Int'l, vol. 72, pp. 166-175 (2003).

Chen et al. "Effect of Hydrogen Peroxide Bleaching on Bone Mineral/Matrix Ratio," Appl. Spectrosc., 56:1035-1037 (2002).

Chen et al., "Bone tissue ultrastructural defects in a mouse model for osteogenesis imperfecta: a Raman spectroscopy study," Proc. SPIE, 5321:85-92 (2004).

Crane et al., "Study of Localization of Response to Fibroblast Growth Factor-2 in Murine Calvaria Using Raman Spectroscopic Imaging," Proc. SPIE, 5321:242-249 (2004).

Dehring et al., "Identifying Chemical Changes in Subchondral Bone Taken from Murine Knee Joints Using Raman Spetroscopy," Applied Spectroscopy, 60(10):1134-41 (2006).

Finney et al., "Ultrastructural elastic deformation of cortical bone tissue probed by NIR Raman spectroscopy," Proc. SPIE, 5321:233-241 (2004).

InPhotonics, Technical Note #13, "Background Filtering in Fiber Optic Raman Sampling Probes," 1999, 2 pages.

International Preliminary Examination Report for Application No. PCT/US2004/020858, dated Jan. 3, 2006.

International Preliminary Examination Report for Application No. PCT/US2004/044038, dated Mar. 20, 2007.

Kale et al., "Three-dimensional cellular development is essential for ex vivo formation of human bone," Nature Biotechnology, 18:954-958 (2000).

Kozloff et al., "Brittle IV Mouse Model for Osteogenesis Imperfecta IV Demonstrates Postpubertal Adaptations to Improve Whole Bone Strength," J. Bone Miner. Res.,19:614-622 (2004).

Lin et al., "Bone metastatic LNCaP-derivative C42B prostate cancer cell line mineralizes in vitro," The Prostate, 47212-221 (2001).

Matousek et al., "Subsurface Probing in Diffusely Scattering Media Using Spatially Offset Raman Spectroscopy," App. Spectroscopy, 59(4):393-400 (2005).

Morris et al., "Application of high pressure Raman spectroscopy to bone biomechanics," Proc. SPIE, 4958:88-97 (2003).

Morris et al., "Bone tissue ultrastructural response to elastic deformation probed by Raman spectroscopy," Faraday Discuss., 126:159-168 (2004).

Morris et al., "Compatibility of Staining Protocols for Bone Tissue with Raman Imaging," Calcif. Tissue Internat., 74:86-94 (2004).

Morris et al., "Raman spectroscopy of early mineralization of normal and pathologic calvaria as revealed by. Raman spectroscopy," Proc. SPIE, 4614:28-39 (2002).

Morris et al., "Kerr-gated picosecond Raman spectroscopy and Raman photon migration of equine bone tissue with 400-nm excitation," Proc. SPIE, 5321:164-169 (2004).

Morris et al., "Raman Imaging as a Probe of Chemical and Biomechanical Properties of Bone Tissue," Proc. SPIE, 3918:2-8 (2000).

Morris et al., "Recent Developments in Raman and Infrared Spectroscopy and Imaging of Bone Tissue," Spectroscopy, 18:155-163 (2004).

Motz et al., "Optical fiber probe for biomedical Raman spectroscopy," Applied Optics, vol. 43, No. 3, pp. 542-554 (2004).

Office Action for U.S. Appl. No. 10/879,797, dated Jan. 18, 2008.
Office Action for U.S. Appl. No. 10/879,797, dated Jun. 1, 2009.
Office Action for U.S. Appl. No. 10/879,797, dated Jun. 27, 2007.
Office Action for U.S. Appl. No. 10/879,797, dated Sep. 29, 2008.
Office Action for U.S. Appl. No. 10/944,518, dated Apr. 23, 2007.
Office Action for U.S. Appl. No. 10/944,518, dated Feb. 28, 2008.
Office Action for U.S. Appl. No. 10/944,518, dated Jun. 1, 2009.
Office Action for U.S. Appl. No. 10/944,518, dated Oct. 2, 2007.
Office Action for U.S. Appl. No. 10/944,518, dated Sep. 30, 2008.

Penel et al., "Composition of Bone and Apatitic Biomaterials as Revealed by Intravital Raman Microspectroscopy," Bone, 36:893-901 (2005).

Penel et al., "MicroRaman Spectral Study of the PO4 and CO3 Vibrational Modes in Synthetic and Biological Apatites," Calcif. Tissue Int., 63:475-481 (1998).

Pfefer et al., "Multiple-fiber probe design for fluorescence spectroscopy in tissue," Applied Optics, vol. 41, No. 22, pp. 4712-4721 (2002).

Rehman et al., "Structural Evaluation of Human and Sheep Bone and Comparison with Synthetic Hydroxyapatite by FT-Raman Spectroscopy," J. Bio. Mat. Res., 29:1287-1294 (1995).

Shea et al., "Bone tissue fluorescence reduction for visible laser Raman spectroscopy," Appl. Spectrosc, 56:182-186 (2002).

Skoog et al., Principles of Instrumental Analysis, 4th ed., p. 296-309 (Saunders College Publishing 1992).

Smith et al., "Fourier Transform Raman Spectroscopic Studies of Human Bone," J. Mat. Sci., 5:775-778 (1995).

Smukler et al., "Analysis of Normal Murine Cartilage Using Raman Spectroscopy," Poster Session at Internal Medicine Research Day, Dept. of Internal Medicine, University of Michigan, Jun. 2003, 19 pages.

Stewart et al., "Trends in early mineralization of Murine calvarial osteoblastic cultures. A Raman Microscopic Study," J. Raman Spectrosc., 33:536-543 (2002).

Tarnowski et al., "Earliest Mineral and Matrix Changes in Force-Induced Musculoskeletal Disease as Revealed by Raman Microspectroscopic Imaging," J. Bone Miner Res., 19:64-71 (2004).

Timlin et al., "Spatial Distribution of Phosphate Species in Mature and Newly Generated Mammalian Bone by Hyperspectral Raman Imaging," J. Biomedical Optics 4(1), 28-34 (1999).

U.S. Appl. No. 60/669,880, filed Apr. 11, 2005. Matousek et al., "Apparatus for Depth-Selective Raman Spectroscopy".

Walters et al., "A Raman and Infrared Spectroscopic Investigation of Biological Hydroxyapatite," J. Inorg. Biochem., 39:193-200 (1990).

Widjaja et al., "Band-Target Entropy Minimization (BTEM) Applied to Hyperspectral Raman Image Data," Appl. Spectrosc., 57:1353-1362 (2003).

Widjaja et al., "Thermal perturbations to bone mineral crystal structure studied by Raman and NMR spectroscopies," Proc. SPIE , 5321:223-232 (2004).

* cited by examiner

METHOD AND APPARATUS FOR EVALUATING CONNECTIVE TISSUE CONDITIONS

STATEMENT REGARDING FEDERALLY SPONSORED RESEARCH OR DEVELOPMENT

This invention was made with Government support under Grant numbers P30 AR46024, R01 AR34399, and R01 AR47969 awarded by the Public Health Service division of the Department of Health and Human Services, and Grant number T32 AR07080, awarded by the National Institute of Arthritis and Musculoskeletal and Skin Disease, National Institutes of Health. The Government may own certain rights in this invention.

FIELD OF THE DISCLOSURE

The present disclosure generally relates to medical diagnostic apparatus and methods, and more particularly to apparatus and methods that may be used to help diagnose conditions of connective tissue.

BACKGROUND

Osteoporosis is an important healthcare problem. It is estimated that 24 million Americans are affected by osteoporosis and that osteoporosis led to $13.8 billion in healthcare costs in 1995. The risk of dying from hip fracture complications is the same as the risk of dying from breast cancer. For Caucasian females over 50, the risk of hip, spine, or distal forearm fractures is 40%. Osteoporosis is currently defined as a condition in which bone mineral density is greater than two standard deviations below the mean of a young healthy population.

Current techniques for screening individuals for fracture susceptibility are relatively inaccurate and/or pose risks to the patient. For example, the present preferred technique for diagnosis of osteoporosis is dual X-ray absorption (DXA), which measures the amount of mineral in the bone. In some patients, however, a low mineral content does not appear to lead to an increased risk of fracture. Additionally, DXA requires that the patient is exposed to ionizing radiation.

Osteoarthritis is another important health care problem. It has been estimated that 40 million Americans and 70 to 90 percent of persons older than 75 years are affected by osteoarthritis. The prevalence of osteoarthritis among men and women is equal, though its symptoms occur earlier in women. Risk factors include age, joint injury, obesity, and mechanical stress.

Studies suggest physio-chemical alteration of the articular cartilage surface is an early event in the pathogenesis of osteoarthritis. The changes involve physical damage to structural matrix proteins, mediated by physical forces and degradative enzymes.

Current techniques for diagnosing or ruling out osteoarthritis include taking an X-ray image of a joint, analyzing blood samples, and analyzing synovial fluid withdrawn from the joint with a needle. The diagnosis is largely clinical because radiographic findings do not always correlate with symptoms. An X-ray image of a joint may indicate osteoarthritis if a normal space between the bones in a joint is narrowed, an abnormal increase in bone density is evident, or if bony projections or erosions are evident. A blood sample may indicate osteoarthritis if byproducts of hyaluronic acid are present. Hyaluronic acid is a joint lubricant and the presence of its byproducts in the blood may indicate the lubricant's breakdown, a sign of osteoarthritis. Also, elevated levels of a factor called C-reactive protein, which is produced by the liver in response to inflammation, may indicate osteoarthritis. On the other hand, elevated levels of rheumatoid factor and so-called erythrocyte sedimentation rates may indicate rheumatoid arthritis rather than osteoarthritis. An analysis of synovial fluid withdrawn from the joint may indicate osteoarthritis if cartilage cells are present in the fluid. On the other hand, a high white blood cell count in the synovial fluid is an indication of infection, and high uric acid in the synovial fluid is an indication of gout.

SUMMARY

Methods and apparatus are provided for evaluating a connective tissue condition of a patient (e.g., a disease, a risk of developing a disease, a risk of developing a fracture, etc.). For example, an indicator associated with the connective tissue condition may be generated. First, tissue at a first location of the body of the patient is irradiated using a light source. The tissue may be irradiated in vivo through the skin or via an incision, for example. Alternatively, a biopsy of the tissue may be irradiated. Then, spectral content information for light scattered, reflected, or transmitted by the irradiated tissue is determined. The spectral content information may be used, at least in part, to generate an indicator associated with a condition of connective tissue at a second location of the body of the patient, the second location remote from the first location. As just one example, ocular tissue, ear tissue, nasal tissue, etc., may be irradiated and the generated indicator may be associated with a condition of cartilage tissue in a joint such as a knee, an elbow, hip, etc. The indicator may assist a physician in diagnosing or ruling out the connective tissue condition. Also, the indicator may assist in estimating a risk of fracture, estimating a risk of developing a connective tissue disease, monitoring the progression of a connective tissue disease, monitoring a response to treatment of a connective tissue disease, etc.

In one embodiment, a method for evaluating a connective tissue condition of a patient is provided. The method may comprise irradiating a portion of tissue of the patient using a light source, the tissue at a first location of the body of the patient, and receiving light from the portion of the tissue. The method may also comprise determining spectral content information associated with the received light, and generating, based at least on the spectral content information, an indicator of a connective tissue condition associated with connective tissue at a second location of the body of the patient, the second location remote from the first location.

In another aspect, an apparatus for evaluating a connective tissue condition of a patient is provided. The apparatus may include a light source, and a light receiver to receive light from a portion of tissue of a patient irradiated by the light source, the tissue from a first location of a body of the patient. Additionally, the apparatus may include a spectrum analyzer optically coupled to receive light received by the light receiver, the spectrum analyzer configured to generate spectral content information associated with the received light, and a computing device communicatively coupled to the spectrum analyzer, the computing device configured to generate diagnostic information indicative of a connective tissue condition based at least in part on the spectral content information, the connective tissue condition associated with connective tissue at a second location of the body of the patient, the second location remote from the first location.

Further, methods and apparatus are provided for evaluating an ocular tissue condition of a patient (e.g., a disease, a risk of developing a disease, etc.). For example, an indicator associated with the ocular tissue condition may be generated. First, a portion of ocular tissue of the patient is irradiated using a light source. Then, spectral content information for light scattered, reflected, or transmitted by the ocular tissue is determined. The spectral content information is used, at least in part, to generate the indicator. The indicator may assist a physician in diagnosing or ruling out the ocular tissue condition. Also, the indicator may assist in estimating a risk of developing a disease, monitoring the progression of a disease, monitoring a response to treatment of a disease, determining whether surgery is needed, determining the integrity of ocular tissue before or after transplant, etc.

In another embodiment, a method for evaluating ocular tissue of a patient. The method may comprise irradiating a portion of ocular tissue of the patient using a light source, and receiving light from the portion of the ocular tissue. The method may also comprise determining Raman spectra information associated with the received light, and generating, based at least on the Raman spectra information, an indicator of an ocular tissue condition.

In another aspect, an apparatus for evaluating ocular tissue of a patient is provided. The apparatus may comprise a light source, and a Raman probe to receive light scattered from a portion of ocular tissue of a patient irradiated by the light source. Also, the apparatus may comprise a spectrum analyzer coupled to receive light received by the light receiver and to determine Raman spectra information for the received light, and a computing device coupled to the spectrum analyzer, the computing device configured to generate diagnostic information indicative of an ocular tissue condition based at least in part on the Raman spectra information.

BRIEF DESCRIPTION OF THE DRAWINGS

The features and advantages of the apparatus and methods described herein will be best appreciated upon reference to the following detailed description and the accompanying drawings, in which.

DETAILED DESCRIPTION

Diagnostic Apparatus

Figure 1:
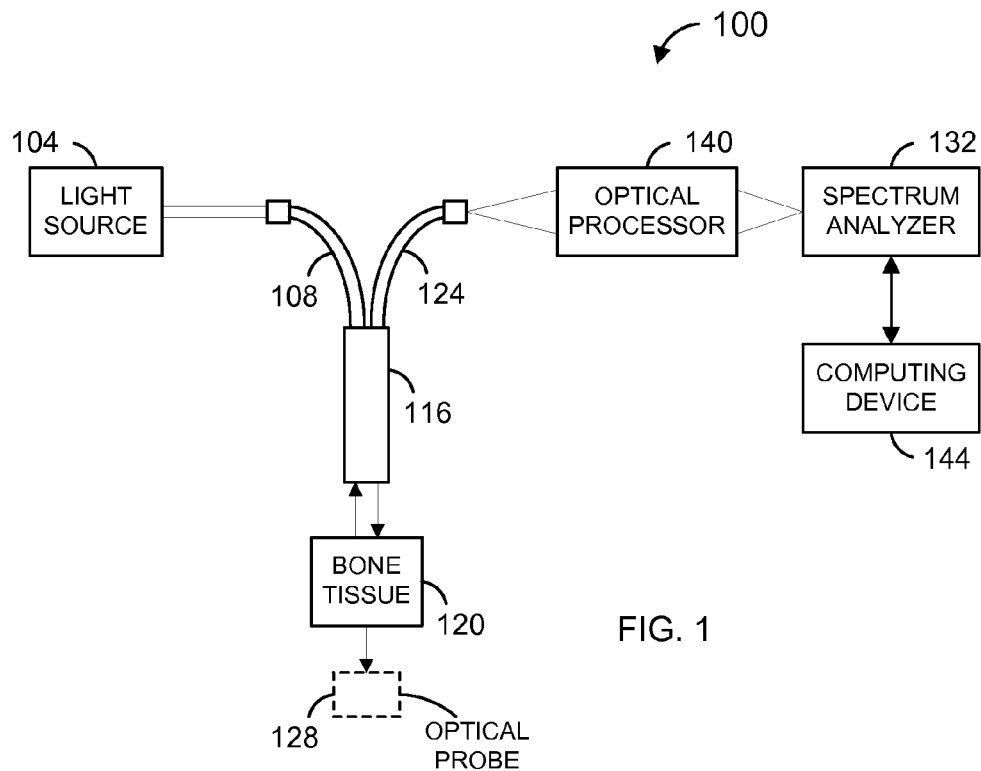
FIG. 1 is a block diagram of one embodiment of an apparatus for determining susceptibility to fracture.

FIG. 1 is a block diagram of an example apparatus 100 that may be used to help diagnose a condition of the bone tissue of a patient. For example, the apparatus 100 may be used to help diagnose osteoporosis, help estimate a susceptibility to fracture of the bone tissue, help diagnose a defect (e.g., osteogenesis imperfecta), help diagnose a nutritional disorder, or help diagnose other disorders related to bone tissue. The apparatus 100 may be used on a patient once, for example, or may be used multiple times over time to help track changes in the bone tissue.

The apparatus 100, which may be used for a Raman spectrometry analysis of a bone tissue or an infrared (IR) analysis of the bone tissue, includes a light source 104 optically coupled to at least one optical fiber 108. For Raman spectrometry, the light source 104 may comprise a laser, for example, that generates substantially monochromatic light. The optical fiber 108 is optically coupled to an optical probe 116. The optical probe 116 may be positioned proximate to a portion of bone tissue 120 from a patient, and may be used to irradiate the bone tissue 120 with the light generated by the light source 104.

In one embodiment, the optical probe 116 is also optically coupled to at least another optical fiber 124. In this embodiment, the optical probe 116 may be used to collect light scattered or reflected by the bone tissue 120 and to transmit the scattered light through the optical fiber 124. This embodiment may be used for Raman spectrometry or for "attenuated total reflection" IR spectrometry.

In another embodiment, another optical probe 128 may be positioned proximate to the portion of the bone tissue 120 such that the optical probe 128 can collect light transmitted by the bone tissue 120. The optical probe 128 may be optically coupled to the optical fiber 124 and can transmit the light transmitted by the bone tissue 120 through the optical fiber 124. This embodiment may be used for "line of sight" IR spectrometry.

The optical fiber 124 is optically coupled to a spectrum analyzer 132 via an optical processor 140 which may include one or more lenses and/or one or more filters. The spectrum analyzer 132 may include, for example, a spectrograph optically coupled to an array of optical detectors, and is communicatively coupled to a computing device 144.

Figure 2:
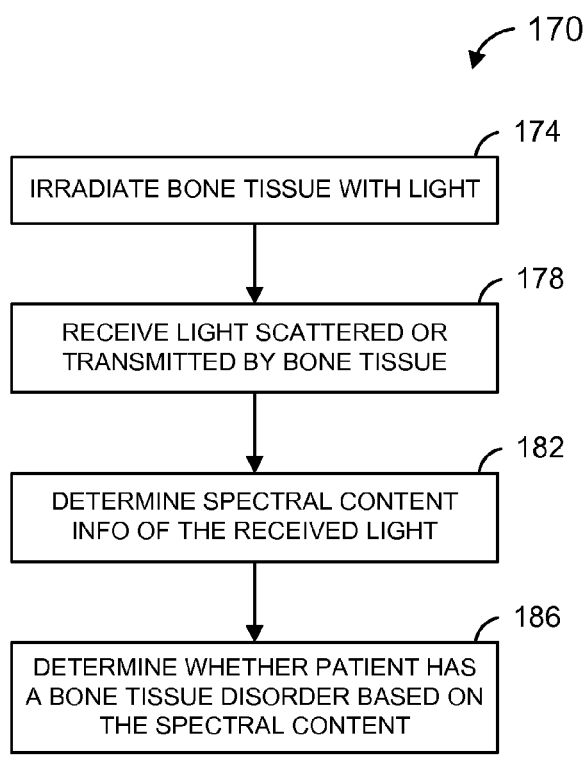
FIG. 2 is a flow diagram of one embodiment of a method for determining a susceptibility to fracture.

FIG. 2 is a flow diagram of a method for determining a condition related to the bone tissue of a patient. The method 170 may be implemented by an apparatus such as the apparatus 100 of FIG. 1, and will be described with reference to FIG. 1. At a block 174, a portion of bone tissue of a patient is irradiated with light. For example, the optical probe 116 may be used to irradiate the bone tissue 120 with light generated by the light source 104. In one embodiment, the bone tissue 120 may be irradiated non-invasively through the skin of the patient. In other embodiments, bone tissue 120 exposed by an incision, or removed as a biopsy, may be irradiated.

In some embodiments, bone tissue at or near a site presumed at risk for fracture (e.g., the hip) may be irradiated. Alternatively, bone tissue not at or near a site of presumed risk may be measured. For in vivo measurements, irradiation may occur at a site at which bone tissue is close to the skin. For example, the proximal diaphysis of the tibia may be irradiated. As biopsy measurements, an iliac crest biopsy could be irradiated as just one example.

At a block 178, light scattered, reflected, or transmitted by the bone tissue may be collected. For example, the optical probe 116 may collect light scattered by the bone tissue 120 (Raman spectrometry). As another example, the optical probe 116 may collect light reflected by the bone tissue 120 ("attenuated total reflection" IR spectrometry). Alternatively, the optical probe 128 may collect light transmitted by the bone tissue 120 ("line of sight" IR spectrometry). As with the optical probe 116, the optical probe 128 may collect light non-invasively through the skin of the patient. In other embodiments, the light may be collected via an incision or collected from an irradiated biopsy.

At a block 182, spectral content information associated with the collected light is generated. For example, the light collected by the optical probe 116 or the optical probe 128 may be provided to the spectrum analyzer 132 via the optical processor 140. The spectrum analyzer 132 may then generate spectral content information associated with the light received by the spectrum analyzer 132.

In Raman spectrometry, the collected light may include light at wavelengths shifted from the wavelength of the incident light. The spectrum of the collected light scattered from bone tissue (referred to hereinafter as the "Raman spectrum of the bone tissue") is indicative of the physico-chemical state of the bone tissue. The Raman spectrum of the bone tissue includes bands indicative of various components of the bone tissue including phosphate of bone mineral, carbonate of bone mineral, interstial water, residual water, hydroxide of the bone mineral, etc. Also included are bands indicative of various components of the collagen matrix of the bone tissue including amide I, hydroxyproline, proline, cross-links, etc. The wavelength at which a band is located is indicative of the component of the bone mineral or matrix to which it corresponds. The height and/or intensity of a band are indicative of the amount of the corresponding component of the bone tissue.

In IR spectrometry, the light generated by the light source 104 includes light at a variety of IR wavelengths. Some of the light at various wavelengths is absorbed by components of the bone tissue, and different components absorb different wavelengths. Thus, similar to the Raman spectrum of the bone tissue, in IR spectrometry, the spectrum of the collected light transmitted by the bone tissue (referred to hereinafter as the "IR spectrum of the bone tissue") includes bands indicative of components and structure of the bone tissue. Unlike in Raman spectrometry, however, the bands in the IR spectrum of the bone tissue are indicative of light absorbed by the bone tissue, rather than light scattered by the bone tissue. Nevertheless, the IR spectrum of the bone tissue is also indicative of the physico-chemical state of the bone tissue. As is known to those of ordinary skill in the art, the Raman spectrum of a bone tissue and an IR spectrum of the same bone tissue may provide indications of different components and/or different structure of the bone tissue.

At a block 186, it is determined whether the patient has a bone tissue disorder based on the spectral content information generated at block 182. For example, the computing device 144 may receive spectral content information from the spectrum analyzer 132. The computing device 144 may then generate an indication of whether the patient has a bone tissue disorder. As another example, the computing device 144 may generate an indication, based on the spectral content information generated at block the 182, that may be used by a physician to determine whether the patient has a bone tissue disorder. For example, the indication may be indicative of a susceptibility of the bone tissue of the patient to fracture. The bone tissue disorder may be, for example, osteoporosis, a genetic disorder (e.g., osteogenesis imperfecta), an acquired disorder, etc.

The determination of the block 186 may be based on additional factors. For example, the determination may be further based on one or more of an age of the patient, a height of the patient, a weight of the patient, a bone mineral density of the patient (e.g., determined using DXA), a family history of the patient, etc. Determining the estimate of susceptibility to fracture will be described in more detail below.

Blocks 174, 178, and 182 may optionally be repeated over a period of time (e.g., weeks, months, years) to generate spectral content information that reflects the condition of the bone tissue of the patient over the period of time. This spectral content information over the period of time may be used in the determination of block 186.

Estimating Susceptibility to Fracture

In one embodiment, the determination of block 186 comprises estimating a susceptibility of the bone tissue of the patient to fracture. Examples of techniques for estimating a susceptibility to fracture based on spectral content information are provided below. Many other techniques may be employed as well. In general, embodiments of methods for estimating susceptibility to fracture may vary according to the environment in which they are to be used. For example, different embodiments may be used in a clinical setting as compared to a laboratory setting because signal-to-noise ratios likely will be higher in the laboratory setting as compared to the clinical setting.

In some embodiments in which Raman spectrometry is employed, the area under a band or height of particular bands in the Raman spectrum of the bone tissue may be used to determine a susceptibility to fracture.

Amide I and amide III are observable in both IR and Raman spectrometry. Amide I and amide III spectra include information similarly indicative of the structure of collagen in the bone tissue, although amide I appears to produce more intense bands as compared to amide III. In Raman spectrometry, amide I of bone tissue is associated with a plurality of bands that can extend over much of the 1600 $cm^{-1}$ to 1700 $cm^{-1}$ region. For example, amide I of bone tissue is associated with a band approximately at 1650 $cm^{-1}$ and a band approximately at 1680 $cm^{-1}$ to 1690 $cm^{-1}$.

It is believed that the absence of collagen intrafibral cross-links weakens bone tissue. The disruption or absence of collagen cross-links can result in changes to the relative intensities of the bands associated with amide I. For example, denaturing collagen to gelatin causes the high frequency shoulder associated with amide I to become more prominent.

Additionally, the intrafibral cross-links in bone matrix collagen cause shifts in the proline bands (proline-2 and proline-3) from 1660 cm$^{-1}$ to 1663 cm$^{-1}$ and from 1670 cm$^{-1}$ to 1690 cm$^{-1}$ respectively. Research has shown that the 1690 cm$^{-1}$ band intensity in bone matrix increases relative to the intensity of the 1663 cm$^{-1}$ band when dehydrodihydroxylysinonorleucine, dehydrohydroxylysinonorleucine or dehydrohistindohydroxymerodesmosine cross-links are chemically reduced. Further research with fetal murine calvarial tissue has shown that the matrix amide I band in newly deposited tissue has a prominent shoulder at approximately 1690 cm$^{-1}$ that becomes smaller as the tissue ages and cross-links are formed.

Figure 3:
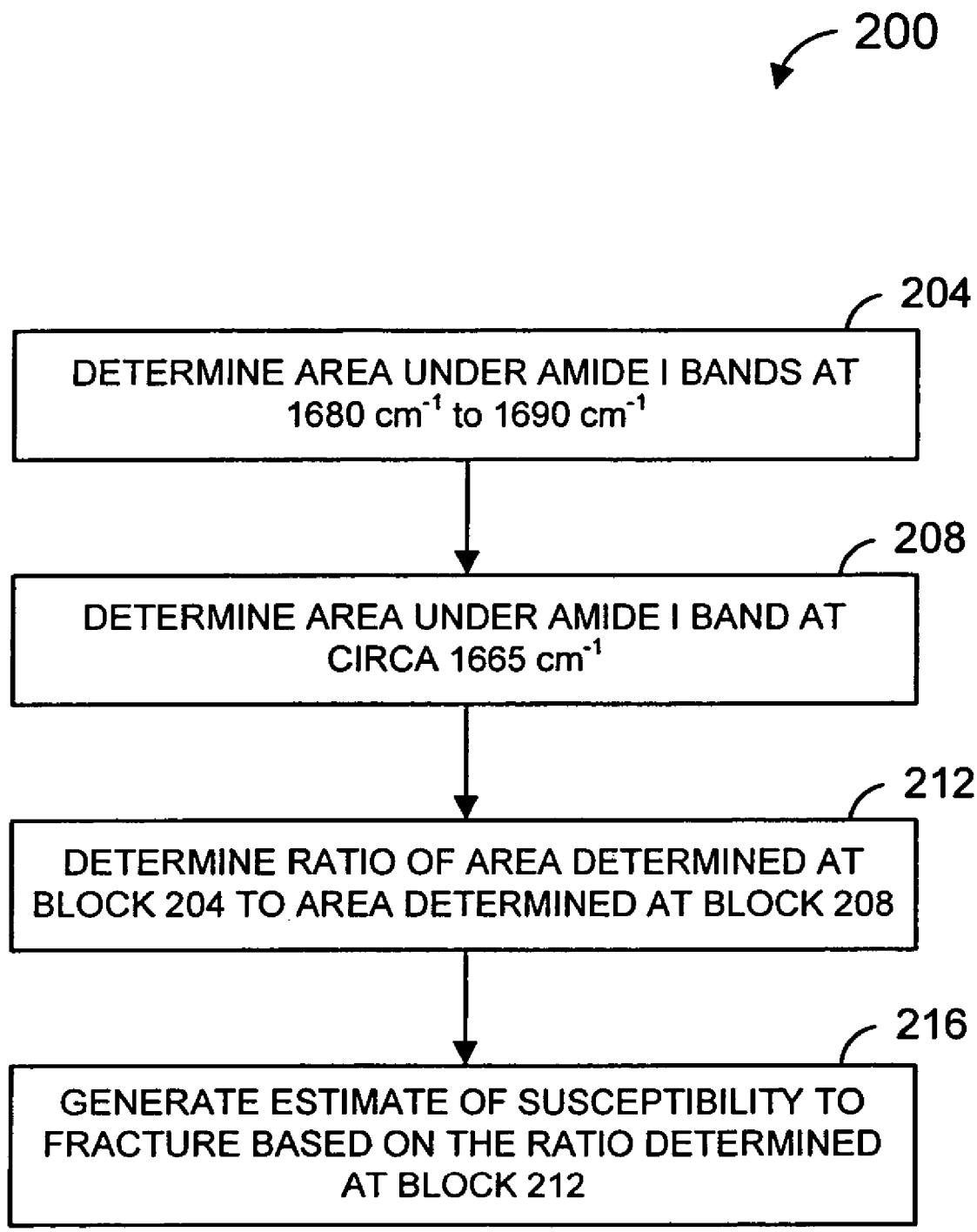
FIG. 3 is a flow diagram of one embodiment of a method for determining a susceptibility to fracture based on spectral content information.

FIG. 3 is a flow diagram illustrating one embodiment of a method for determining susceptibility to fracture based on areas of particular bands in a Raman spectrum of bone tissue. A similar technique may be employed for use with an IR spectrum of bone tissue.

At a block 204, an area of the amide I bands substantially between 1680 cm$^{-1}$ and 1690 cm$^{-1}$ is determined. Determining the area of these amide I bands may include curve fitting using a function such as a mixed Gaussian-Lorentzian function. Determining the area of the bands may also include measuring the area without curve fitting. For example, the area could be measured based on the raw data. As another example, the raw data could be filtered (e.g., with a smoothing filter), and the area could be measured based on the filtered data. In general, the areas under one or more bands may be determined using any of a variety of techniques, including known techniques. At a block 208, an area of the amide I band approximately at 1665 cm$^{-1}$ is determined. Determining the area of this amide I band may be performed in the same or similar manner as described with reference to block 204.

At a block 212, a ratio of the area determined at the block 204 with the area determined at the block 208 may be determined. Then, at a block 216, an estimate of the susceptibility to fracture of the bone tissue is determined based on the ratio determined at the block 212. Determining the estimate of the susceptibility to fracture may comprise determining in which of one or more sets of values the ratio falls. In one embodiment, the estimate of the susceptibility to fracture may comprise an indication of whether or not the bone tissue is susceptible to fracture. In other embodiments, the estimate of the susceptibility to fracture may additionally comprise an indication of one of a plurality of risk levels (e.g., high risk, increased risk, normal risk).

As described previously, the estimate of the susceptibility to fracture determined at the block 216 may be based on additional factors such as one or more of an age of the patient, a height of the patient, a weight of the patient, a bone mineral density of the patient, a family history of the patient, etc.

Figure 4:
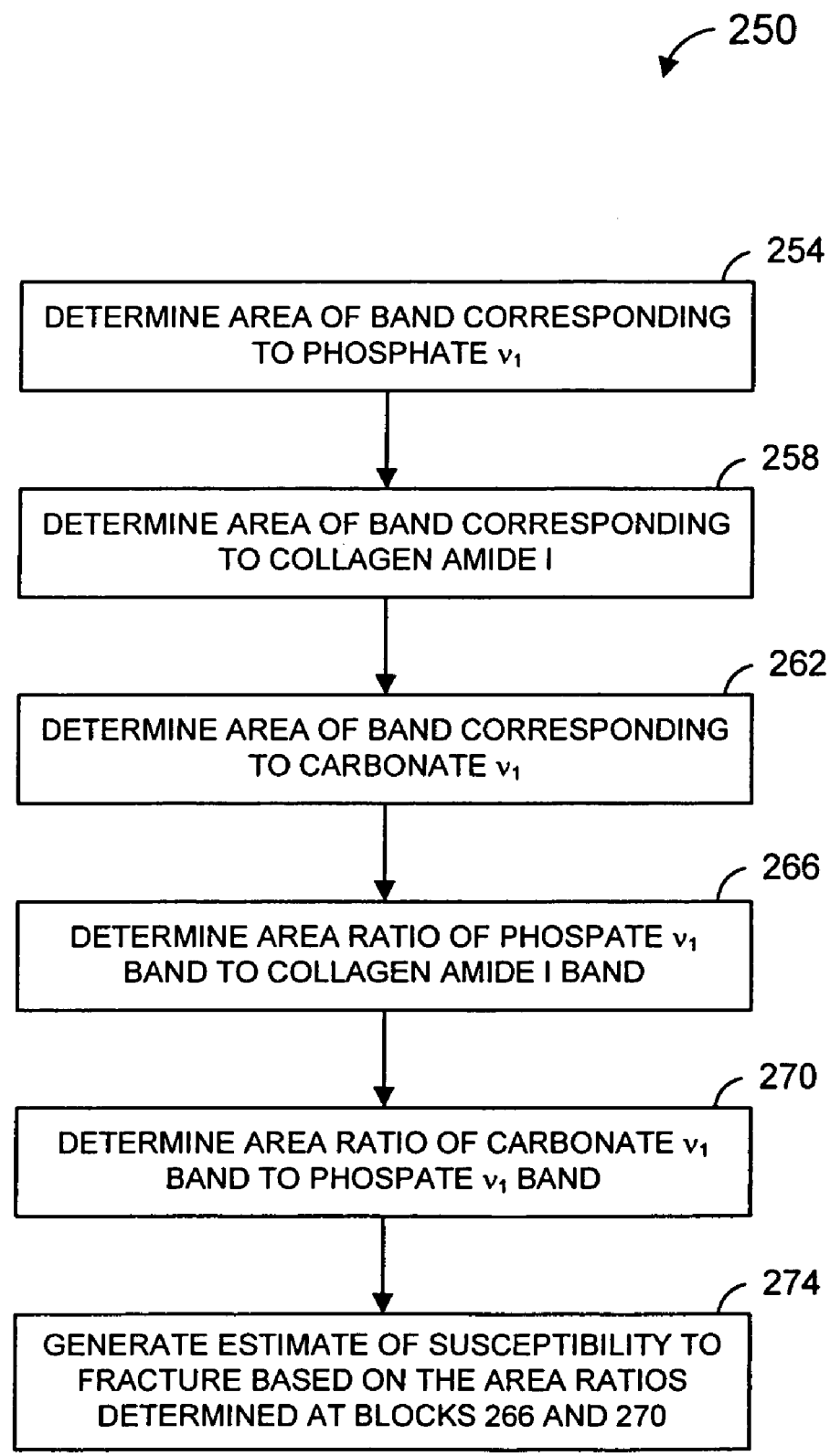
FIG. 4 is a flow diagram of another embodiment of a method for determining a susceptibility to fracture based on spectral content information.

FIG. 4 is a flow diagram illustrating another embodiment of a method for determining susceptibility to fracture based on areas of particular bands. At a block 254, an area of a band associated with phosphate $v_1$ and having a peak at approximately 957 cm$^{-1}$ and having a shoulder at approximately 945 cm$^{-1}$ is determined. Other phosphate bands could be used, although it is believed that the $v_1$ band is more intense than other phosphate bands. Determining the area of this phosphate $v_1$ band may include curve fitting to resolve the phosphate $v_1$ band into two components using a function such as a mixed Gaussian-Lorentzian function or some other suitable function. In general, the area of this band may be performed using any of a variety of techniques, including known techniques such as those described previously. v1

At a block 258, the area of the collagen amide I envelope (the plurality of bands between approximately 1600 cm$^{-1}$ to 1700 cm$^{-1}$) is determined. Other matrix bands could be used, for example bands indicative of hydroxyproline (853 cm$^{-1}$), proline (919 cm$^{-1}$), etc. Determining the area of the collagen amide I band may be performed in the same or similar manner as described previously. At a block 262, the area of the carbonate $v_1$ band (circa 1070 cm$^{-1}$) is determined. Determining the area of the carbonate $v_1$ band may be performed in the same or similar manner as described previously. Additionally, other carbonate bands could be used, although it is believed that the $v_1$ band is more intense than other carbonate bands.

At a block 266, a ratio of the area of the phosphate $v_1$ band to the area of the collagen amide I bands is determined. At a block 270, a ratio of the area of the carbonate $v_1$ band to the area of phosphate $v_1$ band is determined. It is believed that this ratio is a rough measure of the size and crystallinity of mineral crystals.

Figure 5:
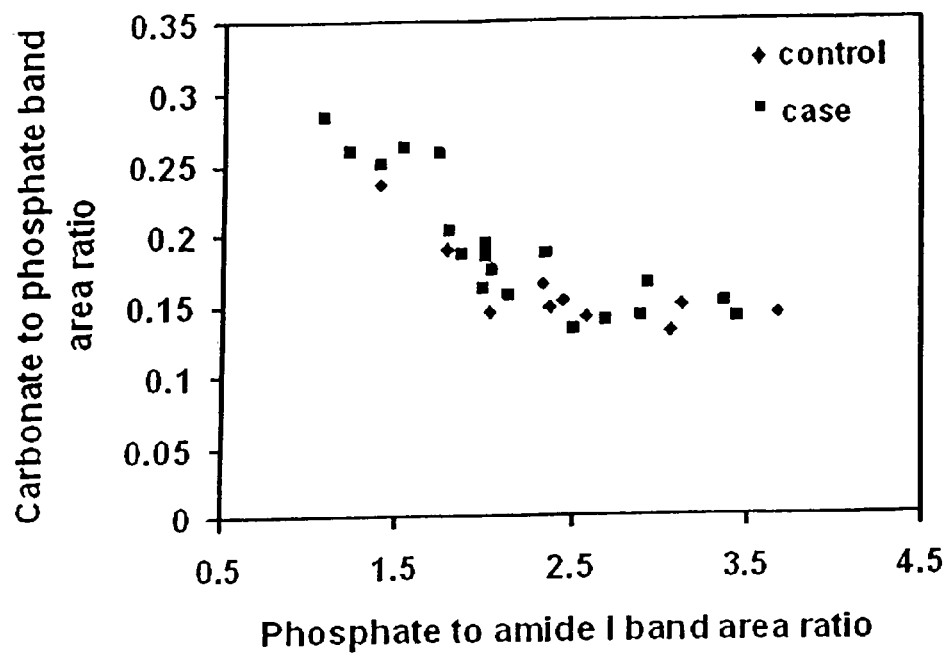
FIG. 5 is a chart showing measured spectral content information for a group of patients that suffered fractures and for a control group.

FIG. 5 is a plot of the above-described ratios determined from bone tissue taken from the proximal femur in the same location for each individual in a matched set of females. A control group included eleven individuals who had died without having a hip fracture. A fracture group included eighteen individuals who had sustained a hip fracture and were treated with arthroplasty. In the fracture group, those who had sustained fracture due to trauma such as automobile accidents or falls from a ladder were excluded. The control group and the fracture group were selected such that the age of the individuals and the bone volume fractions were similar between the two groups.

As can be seen in FIG. 5, a relationship exists between the carbonate/phosphate ratio and the phosphate/amide I ratio. As the phosphate/amide I ratio decreases, the carbonate/phosphate ratio at first generally remains approximately constant. As the phosphate/amide I ratio continues to decrease, the carbonate/phosphate ratio then tends to increase considerably. The fracture specimens tend to be concentrated at the low end of the phosphate/amide I ratio range, while the control specimens tend to be concentrated at the upper end of the phosphate/amide I ratio range. A low phosphate/amide I ratio and a high carbonate/phosphate ratio appear strongly associated with hip fracture. Student t-tests were conducted on the data illustrated graphically in FIG. 4. A comparison of the carbonate/phosphate ratios between the two groups (the fracture group and the control group) resulted in a p-value of 0.08. A comparison of the phosphate/collagen ratios between the two groups resulted in a p-value of 0.28.

Referring again to FIG. 4, at a block 274, an estimate of the susceptibility to fracture of the bone tissue is determined based on the ratios determined at the blocks 266 and 270. Determining an estimate of the susceptibility to fracture may comprise determining whether the ratios determined at the blocks 266 and 270 fall within one or more sets of values. Additionally, in one embodiment, the estimate of the susceptibility to fracture may comprise an indication of whether or not the bone tissue is susceptible to fracture. In other embodiments, the estimate of the susceptibility to fracture may additionally comprise an indication of one of a plurality of risk levels (e.g., high risk, increased risk, normal risk).

The estimate of the susceptibility to fracture determined at the block 274 may be based on additional factors such as one or more of an age of the patient, a height of the patient, a weight of the patient, a bone mineral density of the patient, a family history of the patient, etc. Additionally, the estimate of the susceptibility to fracture determined at block 274 may be based on spectral content information taken over a period of time (e.g., weeks, months, years).

Other information in the IR spectrum or the Raman spectrum of the bone tissue can be used in addition to, or as an alternative, the information described above. For example, information related to bands other than those described above could be used. Additionally, information related to the width, shape (e.g., whether or not a band has "shoulders"), height, etc. of particular bands could be used in determining susceptibility to fracture. Additionally, more sophisticated analyses could be employed such as a cluster analysis.

In a study separate from the study associated with the data of FIG. 5, iliac crest biopsies were analyzed from ten subjects without fractures (mean age 56 years, range 43-70 years) and five subjects with osteoporotic fractures (mean age 63 years, range 50-72 years). In particular, for each specimen, trabecular and cortical regions were scanned using Raman spectroscopy and average carbonate/phosphate and phosphate/amide I band area rations were obtained for the trabecular and cortical regions. No corrections were made for multiple comparisons.

Both carbonate $v_1$/phosphate $v_1$ ratio and phosphate $v_1$/amide I ratio were higher in cortical than trabecular bone for all specimens (p=0.005 and p=0.01, respectively, paired t-tests). This may suggest that mineralized matrix chemistry differs between bone types due to, for example, a fundamental difference or a result of differing average tissue age. Chemical composition of cortical bone mineralized matrix appears to change with age, as demonstrated by a decrease in phosphate/amide I ratio (p=0.005, linear regression model). Neither carbonate $v_1$/phosphate $v_1$ ratio in cortical bone nor any measure in trabecular bone showed significant change with age. The phosphate $v_1$/amide I ratio in patients without fractures was greater in cortical than trabecular bone until age 55 (in all 6 subjects), but greater in trabecular bone in those 55 y or older (in all 4 subjects). In all 5 patients with fractures, the phosphate $v_1$/amide I ratio was greater in cortical bone. Thus, patients with fractures demonstrated the pattern seen in younger (under 55) non-fractured subjects, as opposed to the pattern of patients of similar age without fractures. It is possible that failure to alter mineralized matrix chemistry results in increased fracture risk. Another possibility is that the greater phosphate $v_1$/amide I ratio in cortical bone for patients with fractures, as compared to phosphate $v_1$/amide I ratio in the trabecular bone, was a result of the fracture. There may be other explanations as well for the differences in the relationship between phosphate $v_1$/amide I ratio in cortical bone and trabecular bone between patients with fractures and patients without fractures.

Comparing patients with fractures to patients without fractures, trabecular bone from patients with fractures had a lower phosphate $v_1$/amide I ratio (p=0.03, t-test). No differences appeared to be found in cortical bone or in carbonate $v_1$/phosphate $v_1$ ratio in trabecular bone. This lower mineral/matrix ratio (decreased mineral) in trabecular bone with patients with fractures may suggest a systemic increase in remodeling prior to or following fracture, and is likely demonstrated more clearly in trabecular bone because of its more rapid turnover. If this increase in remodeling occurs prior to fracture, chemical composition from iliac crest biopsy specimens may improve fracture risk assessment. The lower phosphate $v_1$/amide I ratio in trabecular bone for patients with fractures, however, could be a result of the fracture. There may be other explanations as well for the lower phosphate $v_1$/amide I ratio in trabecular bone for patients with fractures.

Yet another study was conducted that was designed to help understand whether, and how, the chemical composition of the bone extracellular matrix changes immediately after fracture. Raman spectroscopy was used to compare chemical composition between the fracture site and a location away from the fracture site. With this experimental model, it was assumed that there was originally no difference along the length of the bone. It was also assumed that there was little change far from the fracture site as a result of the fracture. Thus, differences in chemical composition found in this study between the fracture site and far from it may model changes in the chemical composition of the bone as a result of the fractures.

In this study, the tibiae of five mice were fractured in a controlled manner. One day later, the tibiae were dissected out and Raman spectra were obtained for cortical bone at/near the fracture site and approximately 2 mm from the fracture site (no trabecular bone was analyzed). Data from both locations were available for 4 limbs, each from separate animals.

The results indicated a decreased phosphate $v_1$/amide I ratio and increased carbonate $v_1$/phosphate $v_1$ ratio at the fracture site as compared to the site 2 mm away from the fracture. This data may suggest there is some change in the chemical composition of the bone extracellular matrix following fracture. It is important to note, however, that this assumes that there was no difference in chemical composition existed prior to the fracture between the two sites. It also assumes that there was little change at the site 2 mm away from the fracture site as a result of the fracture. There may be other explanations for why the study indicates decreased phosphate $v_1$/amide I ratio and increased carbonate $v_1$/phosphate $v_1$ ratio at the fracture site as compared to the site 2 mm away from the fracture.

Further Description of the Diagnosis Apparatus

In general, embodiments of apparatus for determining a bone tissue disorder may vary in design according to the environment in which they are to be used. For example, an apparatus to be used in a clinical setting may be designed to obtain spectrum information more quickly as compared to an apparatus to be used in a laboratory setting.

Referring again to FIG. 1, many types of light sources 104 may be employed. With regard to Raman spectrometry, a substantially monochromatic light source can be used. In general, near-infrared wavelengths provide better depth of penetration into tissue. On the other hand, as wavelengths increase, they begin to fall outside the response range of silicon photo detectors (which have much better signal-to-noise ratios than other currently available detectors). One example of a light source that can be used is the widely available 830 nanometer diode laser. This wavelength can penetrate at least 1 to 2 millimeters into tissue. Additionally, this wavelength is not absorbed by blood hemoglobin and is only weakly absorbed by melanin. If the bone tissue is to be exposed by incision, or if biopsied bone tissue is to be examined, other wavelengths may be employed. For example, a 785 nanometer diode laser could be used.

Many other wavelengths may be used as well. In general, a wavelength of a light source may be chosen based on various factors including one or more of a desired depth of penetration, availability of photo detectors capable of detecting light at and near the wavelength, efficiency of photo detectors, cost, manufacturability, lifetime, stability, scattering efficiency, penetration depth, etc. Any of a variety of substantially monochromatic light sources can be used, including commercially available light sources. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier.

With regard to IR spectrometry, any of a variety of types of light sources can be used, including commercially available light sources. For example, light sources known to those of ordinary skill in the art as being suitable for analysis of bone tissues can be used.

With regard to the optical probe 116, any of variety optical probes can be used, including commercially available optical probes. For instance, the *Handbook of Vibrational Spectroscopy, Volume 2: Sampling Techniques*, 1587-1597 (J. Chalmers et al. eds., John Wiley & Sons Ltd. 2002) describes examples of fiber optic probes that can be used. For Raman spectrometry, optical probes designed for Raman spectrometry may be used. For example, any of a variety of commercially available fiber optic probes can be used. Some commercially available fiber optic probes include filters to reject Raman scatter generated within the excitation fiber and/or to attenuate laser light entering the collection fiber or fibers. Loosely focused light may help eliminate or minimize patient discomfort as compared to tightly focused light. As is known to those of ordinary skill in the art, loosely focused light may be achieved by a variety of techniques including multimode delivery fibers and a long focal length excitation/collection lens(es).

Existing commercially available fiber optic probes may be modified, or new probes developed, to maximize collection efficiency of light originating at depths of 1 millimeter or more below the surface of a highly scattering medium, such as tissue. Such modified, or newly developed probes, may offer better signal-to-noise ratios and/or faster data collection. The probe may be modified or may be coupled to another device to help maintain a constant probe-to-tissue distance, which may help to keep the system in focus and help maximize the collected signal.

If the bone is to be irradiated via an incision (and/or the light is to be collected via an incision), relay optics may be coupled to, or incorporated in, a needle. For example, two optical fibers or an "n-around-one" array could be used. In general, the size and the number of fibers should be appropriate to fit into a needle. The diameter of the excitation/collection lens or lenses used in such an embodiment could be small to help minimize the size of the incision. For example, lenses of diameters between 0.3 and 1 millimeter could be used. Lenses having larger or smaller diameters could be used as well. The lens(es) and or optical fibers could be incorporated into a hypodermic needle such as a #12 French type needle.

Additionally, a microprobe or microscope (e.g., a modified epi-fluorescence microscope) may be used instead of the optical probe 116 of FIG. 1. In this embodiment, the optical fiber 108 and/or the optical fiber 124 may be omitted.

The optical processor 140 may include one or more lenses for focusing the collected light. The optical processor 140 may also include one or more filters to attenuate laser light. Although shown separate from the spectrum analyzer 132, some or all of the optical processor 140 may optionally be a component of the spectrum analyzer 132.

The spectrum analyzer 132 may comprise a spectrograph optically coupled with a photo detector array. The photo detector array may comprise a charge coupled device, or some other photo detection device. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier.

In another embodiment, the spectrum analyzer 132 may comprise one or more filters to isolate a plurality of wavelengths of interest. Then, one or more photo detectors (e.g., a CCD, an avalanche photodiode, photomultiplier tube, etc.) could be optically coupled to the output of each filter. A single detector could be used with a tunable filter (e.g., an interferometer, liquid crystal tunable filter, acousto-optic tunable filter, etc.) or if fixed passband filters (e.g., dielectric filters, holographic filters, etc.) are placed in front of the detector one at a time using, for example, a slider, filter wheel, etc. In general, any of a variety of spectrum analyzers could be used such as a Raman analyzer, an IR spectrum analyzer, an interferometer, etc.

The computing device 144 may comprise, for example, an analog circuit, a digital circuit, a mixed analog and digital circuit, a processor with associated memory, a desktop computer, a laptop computer, a tablet PC, a personal digital assistant, a workstation, a server, a mainframe, etc. The computing device 144 may be communicatively coupled to the spectrum analyzer 132 via a wired connection (e.g., wires, a cable, a wired local area network (LAN), etc.) or a wireless connection (a BLUETOOTH™ link, a wireless LAN, an IR link, etc.). In some embodiments, the spectral content information generated by the spectrum analyzer 132 may be stored on a disk (e.g., a floppy disk, a compact disk (CD), etc.), and then transferred to the computing device 144 via the disk. Although the spectrum analyzer 132 and the computer 144 are illustrated in FIG. 1 as separate devices, in some embodiments the spectrum analyzer 132 and the computing device 144 may be part of a single device. For example, the computing device 144 (e.g., a circuit, a processor and memory, etc.) may be a component of the spectrum analyzer 132.

FIG. 5 is a block diagram of an example computing device 144 that may be employed. It is to be understood that the computer 340 illustrated in FIG. 5 is merely one example of a computing device 144 that may be employed. As described above, many other types of computing devices 144 may be used as well. The computer 340 may include at least one processor 350, a volatile memory 354, and a non-volatile memory 358. The volatile memory 354 may include, for example, a random access memory (RAM). The non-volatile memory 358 may include, for example, one or more of a hard disk, a read-only memory (ROM), a CD-ROM, an erasable programmable ROM (EPROM), an electrically erasable programmable ROM (EEPROM), a digital versatile disk (DVD), a flash memory, etc. The computer 340 may also include an I/O device 362. The processor 350, volatile memory 354, non-volatile memory 358, and the I/O device 362 may be interconnected via one or more address/data buses 366. The computer 340 may also include at least one display 370 and at least one user input device 374. The user input device 374 may include, for example, one or more of a keyboard, a keypad, a mouse, a touch screen, etc. In some embodiments, one or more of the volatile memory 354, non-volatile memory 358, and the I/O device 362 may be coupled to the processor 350 via one or more separate address/data buses (not shown) and/or separate interface devices (not shown), coupled directly to the processor 350, etc.

The display 370 and the user input device 374 are coupled with the I/O device 362. The computer 340 may be coupled to the spectrum analyzer 132 (FIG. 1) via the I/O device 362. Although the I/O device 362 is illustrated in FIG. 5 as one device, it may comprise several devices. Additionally, in some embodiments, one or more of the display 370, the user input device 374, and the spectrum analyzer 132 may be coupled directly to the address/data bus 366 or the processor 350. Additionally, as described previously, in some embodiments the spectrum analyzer 132 and the computer 340 may be incorporated into a single device.

The previously described additional factors that may be used for diagnosing a bone tissue disorder (e.g., one or more of an age of the patient, a height of the patient, a weight of the patient, a bone mineral density of the patient, a family history of the patient, etc.) may be entered via the user input device 374, loaded from a disk, received via a network (not shown), etc. These additional factors may be stored in one or more of the memories 354 and 358. Additionally, previously measured spectral content information may be loaded from a disk, received via a network (not shown), etc., and stored in one or more of the memories 354 and 358.

A routine, for example, for estimating a susceptibility to fracture based on spectral content information may be stored, for example, in whole or in part, in the non-volatile memory 358 and executed, in whole or in part, by the processor 350. For example, the method 200 of FIG. 3 and/or the method 250 of FIG. 4 could be implemented in whole or in part via a software program for execution by the processor 350. The program may be embodied in software stored on a tangible medium such as CD-ROM, a floppy disk, a hard drive, a DVD, or a memory associated with the processor 350, but persons of ordinary skill in the art will readily appreciate that the entire program or parts thereof could alternatively be executed by a device other than a processor, and/or embodied in firmware and/or dedicated hardware in a well known manner. With regard to the method 200 of FIG. 3 and the method 250 of FIG. 4, one of ordinary skill in the art will recognize that the order of execution of the blocks may be changed, and/or the blocks may be changed, eliminated, or combined.

Although the method 200 of FIG. 3 and the method 250 of FIG. 4 were described above as being implemented by the computer 340, one or more of the blocks of FIGS. 3 and 4 may be implemented by other types of devices such as an analog circuit, a digital circuit, a mixed analog and digital circuit, a processor with associated memory, etc.

Determining Cartilage Conditions

Although the example apparatus described above were described in the context of analyzing bone tissue, these apparatus or similar apparatus can be used to determine conditions associated with other connective tissues. Generally, connective tissue comprises a biological tissue having an extensive extracellular matrix. Connective tissue helps form a framework and/or support structure for body tissues, organs, etc. Examples of connective tissue that can be analyzed include supporting connective tissue (e.g., bone, cartilage, etc.), fibrous connective tissue (e.g., cartilage, tendons, ligaments, etc.), loose connective tissue, adipose tissue, etc.

As described above, connective tissues such as cartilage may be analyzed. At least some spectral information associated with cartilage can be distinguished from spectral information associated with bone, and thus techniques for determining cartilage conditions based on spectral information may be performed in vivo.

Figure 7:
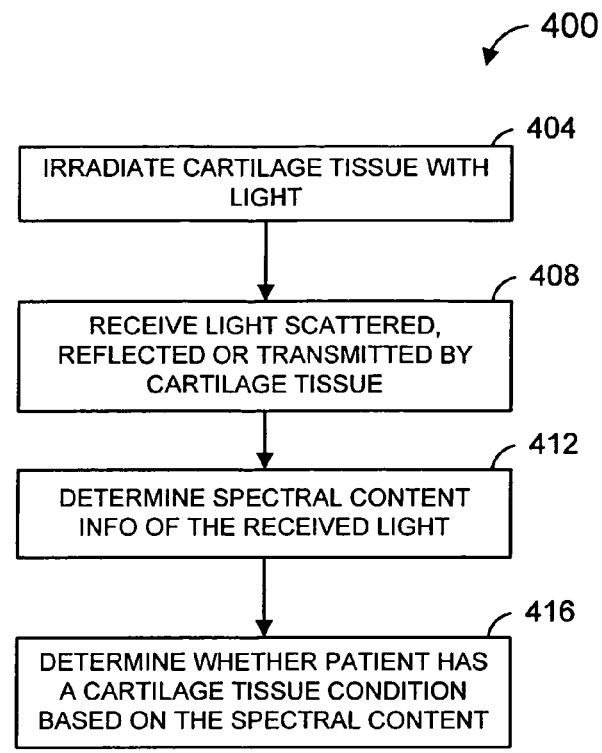
FIG. 7 is a flow diagram of one embodiment of a method for determining a cartilage tissue condition.

FIG. 7 is a flow diagram of an example method for determining a condition related to cartilage tissue of a patient. The method 400 may be implemented by an apparatus such as the apparatus 100 of FIG. 1, and will be described with reference to FIG. 1. At a block 404, a portion of cartilage tissue of a patient is irradiated with light. For example, the optical probe 116 may be used to irradiate the cartilage tissue with light generated by the light source 104. In one embodiment, the cartilage tissue may be irradiated non-invasively through the skin of the patient. In other embodiments, cartilage tissue exposed by an incision, or removed as a biopsy, may be irradiated.

At a block 408, light scattered, reflected, or transmitted by the cartilage tissue may be collected. For example, the optical probe 116 may collect light scattered by the cartilage tissue (Raman spectrometry). As another example, the optical probe 116 may collect light reflected by the cartilage tissue ("attenuated total reflection" IR spectrometry). Alternatively, the optical probe 128 may collect light transmitted by the cartilage tissue ("line of sight" IR spectrometry). As with the optical probe 116, the optical probe 128 may collect light non-invasively through the skin of the patient. In other embodiments, the light may be collected via an incision or collected from an irradiated biopsy.

At a block 412, spectral content information associated with the collected light is generated. For example, the light collected by the optical probe 116 or the optical probe 128 may be provided to the spectrum analyzer 132 via the optical processor 140. The spectrum analyzer 132 may then generate spectral content information associated with the light received by the spectrum analyzer 132.

In Raman spectrometry, the cartilage spectrum of the collected light scattered from cartilage tissue (referred to hereinafter as the "Raman spectrum of the cartilage tissue") is indicative of the physico-chemical state of the cartilage tissue. The Raman spectrum of the cartilage tissue includes bands indicative of various components present in cartilage tissue including phosphate, carbonate, etc. Also included are bands indicative of various components of the collagen matrix of the cartilage tissue including amide I, amide III, etc. The wavelength at which a band is located is indicative of the component of the mineral or matrix to which it corresponds. The height and/or intensity of a band are indicative of the amount of the corresponding component.

Similar to the Raman spectrum of the cartilage tissue, in IR spectrometry, the spectrum of the collected light transmitted by the cartilage tissue (referred to hereinafter as the "IR spectrum of the cartilage tissue") includes bands indicative of components and structure of the cartilage tissue. Unlike in Raman spectrometry, however, the bands in the IR spectrum of the cartilage tissue are indicative of light absorbed by the cartilage tissue, rather than light scattered by the cartilage tissue. Nevertheless, the IR spectrum of the cartilage tissue is also indicative of the physico-chemical state of the cartilage tissue. As is known to those of ordinary skill in the art, the Raman spectrum of a cartilage tissue and an IR spectrum of the same cartilage tissue may provide indications of different components and/or different structure of the cartilage tissue.

At a block 416, it is determined whether the patient has a cartilage tissue condition based on the spectral content information generated at block 412. For example, the computing device 144 may receive spectral content information from the spectrum analyzer 132. The computing device 144 may then generate an indication, based at least in part on the spectral content information, of whether the patient has a cartilage tissue condition. The cartilage tissue condition may be, for example, osteoarthritis, rheumatoid arthritis, chondromalacia, polychondritis, relapsing polychondritis, a genetic disorder, an acquired disorder, etc. Also, the cartilage tissue condition may be an increased risk of developing a disease such as osteoarthritis, rheumatoid arthritis, chondromalacia, polychondritis, etc. A computing device such as the computing device 340 of FIG. 6 may be used to generate the indication. In some embodiments, the computing device 144 may generate, based on the spectral content information generated at block the 412, an indicator associated with the cartilage tissue condition. Such an indicator may be used by a physician to determine whether the patient has a cartilage tissue condition, to monitor the progression of a cartilage tissue condition, to monitor a response to treatment of a cartilage tissue condition, etc.

The determination of the block 416 may be based on additional factors. For example, the determination may be further based on one or more of an age of the patient, a weight of the patient, a history of weight of the patient, a blood test, an analysis of synovial fluid, a medical history of the patient (e.g., past joint injuries), an X-ray, a family history of the patient, etc. Determining whether the patient has a cartilage tissue condition will be described in more detail below.

Blocks 404, 408, and 412 may optionally be repeated over a period of time (e.g., weeks, months, years) to generate spectral content information that reflects the cartilage tissue condition of the patient over the period of time. This spectral content information over the period of time may be used in the determination of block 416.

Evaluating Osteoarthritis Conditions

Examples of techniques for generating an indicator, based on spectral content information, of osteoarthritis are provided below. Many other techniques may be employed as well. In general, embodiments of methods for generating such an indicator may vary according to the environment in which they are to be used. For example, different embodiments may be used in a clinical setting as compared to a laboratory setting because signal-to-noise ratios likely will be higher in the laboratory setting as compared to the clinical setting.

In some embodiments in which Raman spectrometry is employed, the intensity of particular bands in the Raman spectrum of the cartilage tissue may be used to generate an indicator of osteoarthritis. The intensity of a band may be determined by, for example, determining an area under the band or determining a height of the band.

Amide I and amide III are observable in both IR and Raman spectrometry. Amide I and amide III spectra include information similarly indicative of the structure of collagen in the cartilage tissue. In Raman spectrometry, amide III of cartilage tissue is associated with a plurality of bands that can extend over much of the 1240 cm$^{-1}$ to 1270 cm$^{-1}$ region. Also observable are bands associated with minerals present in the cartilage tissue. For example, bands associated with carbonate $v_1$ and phosphate $v_1$ are observable.

Figure 8:
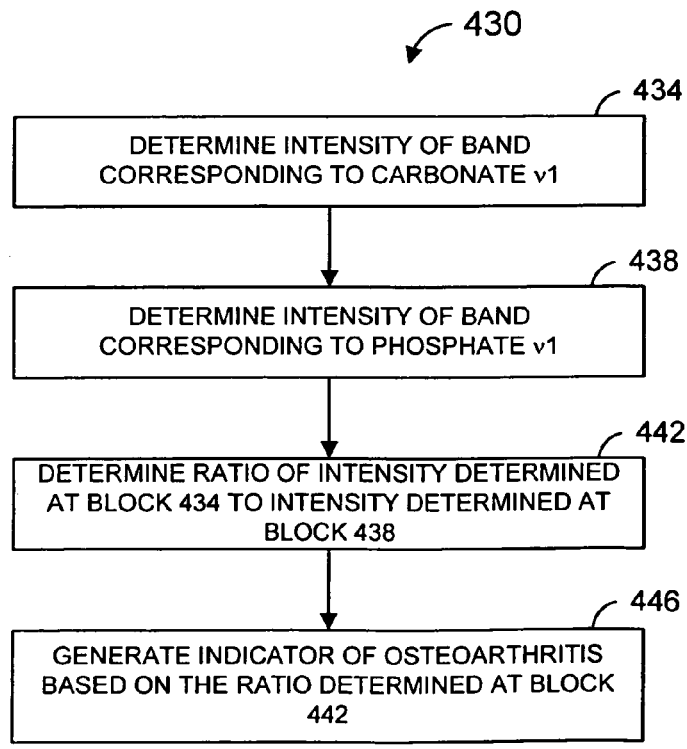
FIG. 8 is a flow diagram of one embodiment of a method for determining a cartilage tissue condition based on spectral content information.

FIG. 8 is a flow diagram illustrating one embodiment of a method 430 for generating an indicator of a cartilage tissue condition based on intensities of particular bands in a Raman spectrum of cartilage tissue. A similar technique may be employed for use with an IR spectrum of cartilage tissue.

At a block 434, an intensity of a carbonate $v_1$ band (nominally located at approximately 1070 cm$^{-1}$) associated with the cartilage tissue is determined. Determining the intensity of this band may include measuring the height of a peak of the band. Also, determining the intensity of this band may include determining the area under the band by curve fitting using a function such as a mixed Gaussian-Lorentzian function. Determining the area of the band may also include measuring the area without curve fitting. For example, the area could be measured based on the raw data. As another example, the raw data could be filtered (e.g., with a smoothing filter), and the height or area could be measured based on the filtered data. In general, the intensity of one or more bands may be determined using any of a variety of techniques, including known techniques. At a block 438, an intensity of a phosphate $v_1$ band (nominally located at approximately 959 cm$^{-1}$) associated with the cartilage tissue is determined. Determining the intensity of this band may be performed in the same or similar manner as described with reference to block 434.

At a block 442, a ratio of the intensity determined at the block 434 with the intensity determined at the block 438 may be determined. Then, at a block 446, an indicator of osteoarthritis is determined based on the ratio determined at the block 446. It is believed that cartilage tissue affected by osteoarthritis has a higher carbonate/phosphate ratio as compared with cartilage not affected by osteoarthritis.

Determining the indicator may comprise determining in which of one or more sets of values the ratio falls by, for example, comparing the ratio to one or more thresholds. In one embodiment, the indicator may comprise an indication of whether or not osteoarthritis is present. In other embodiments, the indicator may comprise one of a plurality of levels indicating a probability or confidence level that osteoarthritis is present. In still other embodiments, the indicator may comprise one of a plurality of levels indicating a risk of developing osteoarthritis. In yet other embodiments, the indicator may comprise one of a plurality of levels indicating a level of severity, a level of progression, etc., of osteoarthritis.

As described previously, the indicator determined at the block 446 may be based on additional factors such as one or more of an age of the patient, a weight of the patient, a prior weight of the patient, blood test data, synovial fluid test data, medical history data (e.g., past joint injuries), X-ray data, family history data, etc.

Figure 9:
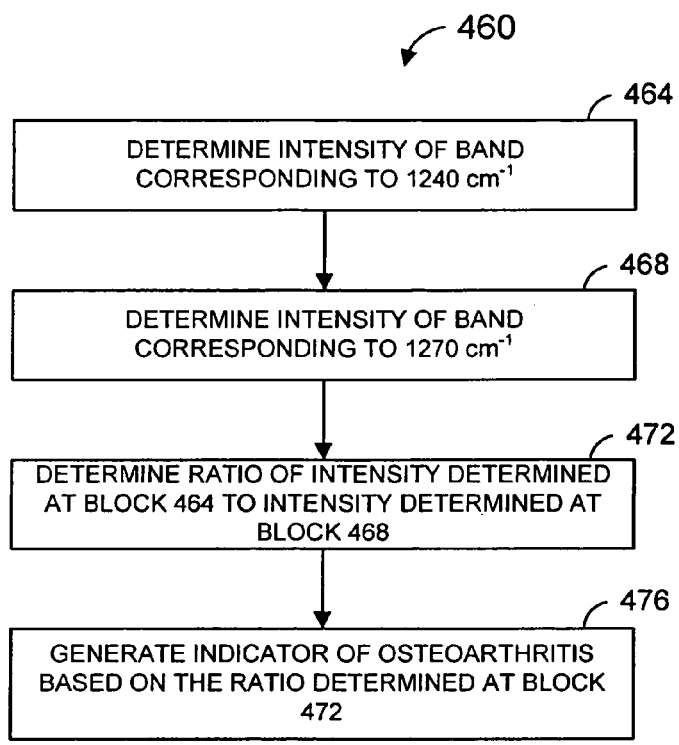
FIG. 9 is a flow diagram of another embodiment of a method for determining a cartilage tissue condition based on spectral content information.

FIG. 9 is a flow diagram illustrating another embodiment of a method 460 for generating an indicator of osteoarthritis based on intensities of particular bands in a Raman spectrum of cartilage tissue. A similar technique may be employed for use with an IR spectrum of cartilage tissue.

At a block 464, an intensity of a band associated with the cartilage tissue having peak nominally at approximately 1240 cm$^{-1}$ is determined. Determining the intensity of this band may be performed in the same or similar manner as described above. At a block 468, an intensity of a band associated with the cartilage tissue having peak nominally at approximately 1270 cm$^{-1}$ is determined. Determining the intensity of this band may be performed in the same or similar manner as described above.

At a block 472, a ratio of the intensity determined at the block 464 with the intensity determined at the block 468 may be determined. Then, at a block 476, an indicator of osteoarthritis is determined based on the ratio determined at the block 472. It is believed that cartilage tissue affected by osteoarthritis has a higher. 1240 cm$^{-1}$ band/1270 cm$^{-1}$ band ratio as compared with cartilage not affected by osteoarthritis.

Determining the indicator may comprise determining in which of one or more sets of values the ratio falls. In one embodiment, the indicator may comprise an indication of whether or not osteoarthritis is present. In other embodiments, the indicator may comprise one of a plurality of levels indicating a probability or confidence level that osteoarthritis is present. In still other embodiments, the indicator may comprise one of a plurality of levels indicating a risk of developing osteoarthritis. In yet other embodiments, the indicator may comprise one of a plurality of levels indicating a level of severity, a level of progression, etc., of osteoarthritis. As described previously, the indicator determined at the block 476 may be based on additional factors.

Figure 10:
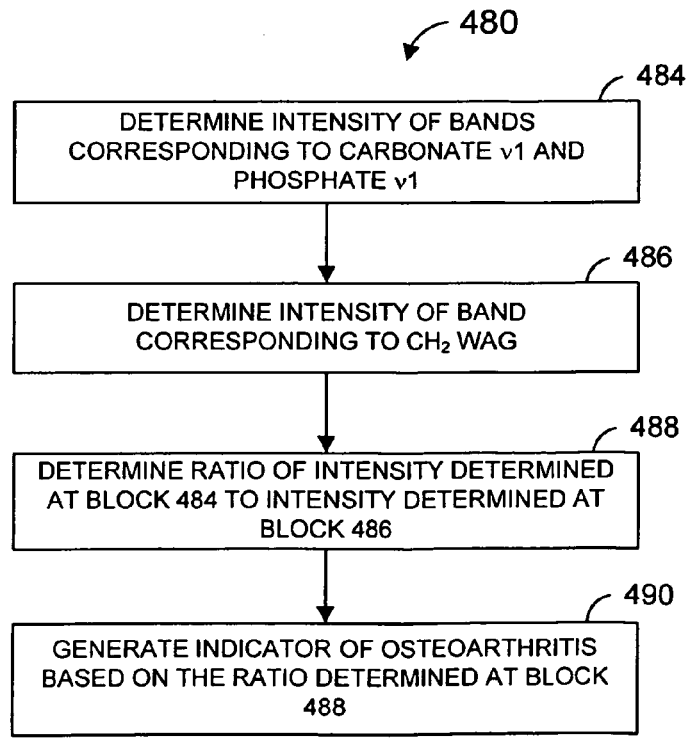
FIG. 10 is a flow diagram of another embodiment of a method for determining a cartilage tissue condition based on spectral content information.

FIG. 10 is a flow diagram illustrating yet another embodiment of a method 480 for generating an indicator of a cartilage tissue condition based on intensities of particular bands in a Raman spectrum of cartilage tissue. A similar technique may be employed for use with an IR spectrum of cartilage tissue.

At a block 484, an intensity of one or more mineral bands associated with the cartilage tissue is determined. For example, the intensity of the carbonate $v_1$ band and the phosphate $v_1$ band may be determined by adding their individual intensities together. Determining the intensity of each individual band in the one or more mineral bands may be performed in the same or similar manner as described above. At a block 486, an intensity of a $CH_2$ wag band associated with the cartilage tissue having peak nominally at approximately 1446 $cm^{-1}$ is determined. Determining the intensity of this band may be performed in the same or similar manner as described above.

At a block 488, a ratio of the intensity determined at the block 484 with the intensity determined at the block 486 may be determined. Then, at a block 490, an indicator of osteoarthritis is determined based on the ratio determined at the block 488. It is believed that cartilage tissue affected by osteoarthritis has a lower mineral/$CH_2$ wag ratio as compared with cartilage not affected by osteoarthritis. With regard to the block 486, other bands associated with the collagen matrix of the cartilage tissue may be used in place of the $CH_2$ wag band such as amide I (1665 $cm^{-1}$), amide III (1240 $cm^{-1}$-1270 $cm^{-1}$), 855 $cm^{-1}$, 880 $cm^{-1}$, 919 $cm^{-1}$, etc. Generally, the ratio determined at the block 486 indicates the amount of mineral per collagen.

Determining the indicator may comprise determining in which of one or more sets of values the ratio falls. In one embodiment, the indicator may comprise an indication of whether or not osteoarthritis is present. In other embodiments, the indicator may comprise one of a plurality of levels indicating a probability or confidence level that osteoarthritis is present. In still other embodiments, the indicator may comprise one of a plurality of levels indicating a risk of developing osteoarthritis. In yet other embodiments, the indicator may comprise one of a plurality of levels indicating a level of severity, a level of progression, etc., of osteoarthritis. As described previously, the indicator determined at the block 490 may be based on additional factors.

In other embodiments, one or more of the methods described above with respect to FIGS. 8-10 may be combined. For example, an indicator of osteoarthritis could be determined based on the ratio determined at the block 442 of FIG. 8 and the ratio determined at the block 472 of FIG. 9. As another example, the indicator of osteoarthritis could be determined based on the ratio determined at the block 442 of FIG. 8 and the ratio determined at the block 488 of FIG. 10. As yet another example, the indicator of osteoarthritis could be determined based on the ratio determined at the block 472 of FIG. 9 and the ratio determined at the block 488 of FIG. 10. As still another example, the indicator of osteoarthritis could be determined based on the ratio determined at the block 442 of FIG. 8, the ratio determined at the block 472 of FIG. 9, and the ratio determined at the block 488 of FIG. 10. Multiple ratios may be used to determine an indicator of osteroarthritis using any of a variety of techniques. As one example, the multiple ratios may be mathematically combined and then the result could be compared to one or more thresholds. As another example, multiple indicators determined based on the multiple ratios could be mathematically combined.

Other information in the IR spectrum or the Raman spectrum of the cartilage tissue can be used in addition to, or as an alternative, the information described above. For example, information related to bands other than those described above could be used. Additionally, information related to the width, shape (e.g., whether or not a band has "shoulders"), height, etc. of particular bands could be used in determining a cartilage tissue condition. Additionally, more sophisticated analyses could be employed such as a cluster analysis, pattern matching, etc.

The locations of particular Raman bands described above with reference to FIGS. 8-10 were determined based on experiments with mouse tissues. One of ordinary skill in the art will recognize that the locations of bands may vary based on, for example, testing error, age, species, etc. For instance, the locations may vary by up to plus or minus 3 $cm^{-1}$, or even more.

Evaluating a Tissue Condition Based on Spectral Analysis of Another Tissue

Spectral content information obtained from one tissue in a first portion of the body may be used to determine a condition associated with tissue in a second portion of the body remote from the first portion. As an example, spectral content information obtained from an eyeball, a nose, an ear, etc., may be used to generate an indicator of osteoarthritis in a hand (including fingers), a foot (including toes), a knee, a hip, a back, a neck, etc. Examples of techniques for generating, based on spectral content information obtained one portion of the body, an indicator of osteoarthritis in another portion of the body are provided below. Many other techniques may be employed as well. In general, embodiments of methods for generating such an indicator may vary according to the environment in which they are to be used. For example, different embodiments may be used in a clinical setting as compared to a laboratory setting because signal-to-noise ratios likely will be higher in the laboratory setting as compared to the clinical setting.

It has been observed that some spectral content obtained from a first tissue of the body may exhibit similarities with a second tissue remote from the first tissue. For example, ocular tissue includes collagen structures, and spectral content information associated with collagen in ocular tissue may be used to determine if a condition exists with respect to cartilage tissue in a joint of a hand, a foot, a back, a neck, a knee joint, a hip joint, etc. As another example, spectral content information associated with cartilage in nose and/or ear may be used to determine if a condition exists with respect to cartilage tissue in a joint of a hand, a foot, a back, a neck, a knee joint, a hip joint, etc.

Figure 11:
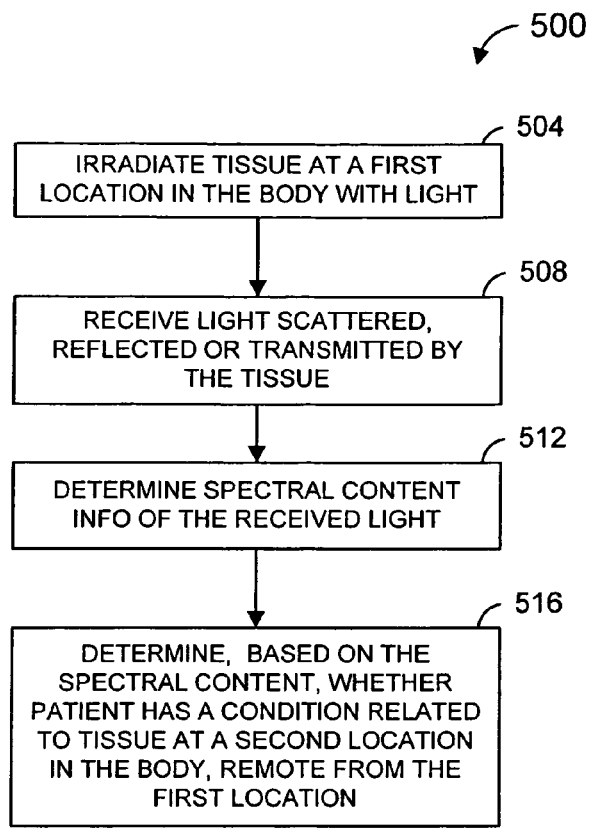
FIG. 11 is a flow diagram of another embodiment of a method for determining a connective tissue condition.

FIG. 11 is a flow diagram of an example method for determining a connective tissue condition. The method 500 may be implemented by an apparatus such as the apparatus 100 of FIG. 1, and will be described with reference to FIG. 1. At a block 504, a portion of connective tissue of a patient is irradiated with light, the connective tissue being at a first location of the patient's body. For example, the optical probe 116 may be used to irradiate the connective tissue with light generated by the light source 104. In one embodiment, the connective tissue may be irradiated non-invasively. For example, ocular tissue may be irradiated. As another example, nasal or ear cartilage may be irradiated through skin or mucus membrane. In other embodiments, connective tissue exposed by an incision, or removed as a biopsy, may be irradiated.

At a block 508, light scattered, reflected, or transmitted by the connective tissue may be collected. For example, the optical probe 116 may collect light scattered by the connective tissue (Raman spectrometry). As another example, the optical probe 116 may collect light reflected by the connective tissue ("attenuated total reflection" IR spectrometry). Alternatively, the optical probe 128 may collect light transmitted by the connective tissue ("line of sight" IR spectrometry). As with the optical probe 116, the optical probe 128 may collect light non-invasively (e.g., through the skin of the patient). In other embodiments, the light may be collected via an incision or collected from an irradiated biopsy, for example.

At a block 512, spectral content information associated with the collected light is generated. For example, the light collected by the optical probe 116 or the optical probe 128 may be provided to the spectrum analyzer 132 via the optical processor 140. The spectrum analyzer 132 may then generate spectral content information associated with the light received by the spectrum analyzer 132.

At a block 516, it is determined whether the patient has a condition related to connective tissue at a second location in the body, remote from the first location, based on the spectral content information generated at block 512. For example, the computing device 144 may receive spectral content information from the spectrum analyzer 132. The computing device 144 may then generate an indication, based at least in part on the spectral content information, of whether the patient has a connective tissue condition regarding connective tissue at the second location. The condition may be a cartilage condition such as osteoarthritis, rheumatoid arthritis, chondromalacia, polychondritis, relapsing polychondritis, a genetic disorder, an acquired disorder, etc. Also, the connective tissue condition may be an increased risk of developing a disease such as osteoarthritis, rheumatoid arthritis, chondromalacia, polychondritis, etc. A computing device such as the computing device 340 of FIG. 6 may be used to generate the indication. In some embodiments, the computing device 144 may generate, based on the spectral content information generated at block the 412, an indicator associated with the connective tissue condition. Such an indicator may be used by a physician to determine whether the patient has a connective tissue condition, to monitor the progression of a connective tissue condition, to monitor a response to treatment of a connective tissue condition, etc.

The determination of the block 516 may be based on additional factors. For example, the determination may be further based on one or more of an age of the patient, a weight of the patient, a history of weight of the patient, a blood test, an analysis of synovial fluid, a medical history of the patient (e.g., past joint injuries), an X-ray, a family history of the patient, etc. Determining whether the patient has a connective tissue condition associated with connective tissue at the second location will be described in more detail below.

Blocks 504, 508, and 512 may optionally be repeated over a period of time (e.g., weeks, months, years) to generate spectral content information that reflects the connective tissue condition of the patient over the period of time. This spectral content information over the period of time may be used in the determination of block 516.

Figure 12:
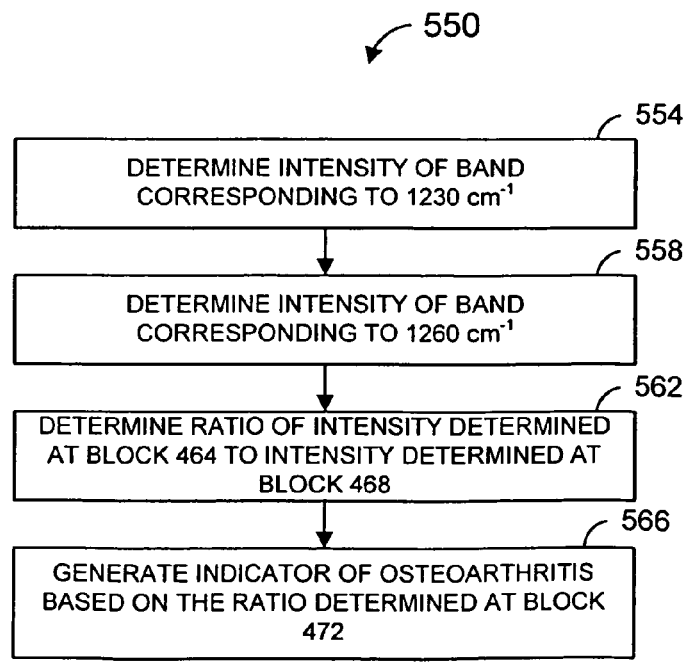
FIG. 12 is a flow diagram of another embodiment of a method for determining a connective tissue condition based on spectral content information.

FIG. 12 is a flow diagram illustrating another embodiment of a method 550 for generating an indicator of osteoarthritis in a cartilage tissue at a first location in the body based on intensities of particular bands in a Raman spectrum of tissue at a second location in the body remote from the first location. A similar technique may be employed for use with an IR spectrum of tissue.

At a block 554, an intensity of a band associated with the tissue having peak nominally at approximately 1230 cm$^{-1}$ is determined. Determining the intensity of this band may be performed in the same or similar manner as described above. At a block 558, an intensity of a band associated with the tissue having peak nominally at approximately 1260 cm$^{-1}$ is determined. Determining the intensity of this band may be performed in the same or similar manner as described above.

At a block 562, a ratio of the intensity determined at the block 554 with the intensity determined at the block 558 may be determined. Then, at a block 566, an indicator of osteoarthritis is determined based on the ratio determined at the block 562. It is believed that ocular tissue, nasal cartilage tissue, ear cartilage tissue, etc., in a person affected by osteoarthritis may have a higher 1230 cm$^{-1}$ band/1260 cm$^{-1}$ band ratio as compared with tissues in a person not affected by osteoarthritis.

Determining the indicator may comprise determining in which of one or more sets of values the ratio falls. In one embodiment, the indicator may comprise an indication of whether or not osteoarthritis is present. In other embodiments, the indicator may comprise one of a plurality of levels indicating a probability or confidence level that osteoarthritis is present. In still other embodiments, the indicator may comprise one of a plurality of levels indicating a risk of developing osteoarthritis. In yet other embodiments, the indicator may comprise one of a plurality of levels indicating a level of severity, a level of progression, etc., of osteoarthritis. As described previously, the indicator determined at the block 566 may be based on additional factors.

Generating the indicator of osteoarthritis may additionally or alternatively comprise other types of analysis of the spectral content information. For example, different ratios such as the ratios described in FIGS. 8, 9, and 10 may be used additionally or alternatively in generating the indicator. In general, the spectral content information obtained from tissue at a first location in the body an indicator of a tissue condition in a connective tissue at a first location in the body and used to generate an indicator of a condition of connective tissue at a second location in the body remote from the first location may depend on the type of tissue at the first location, the type of tissue at the second location, the type of condition, etc.

Evaluating Ocular Tissue

Although examples described above include apparatus and techniques for analyzing bone tissue and cartilage tissue, similar techniques and these apparatus or similar apparatus can be used to determine conditions associated with ocular tissues as well. For example, collagen in ocular tissues may become damaged as a result of natural aging, genetic defects, disease, etc. Alterations to eye collagen may occur before clinical symptoms are evident.

Figure 13:
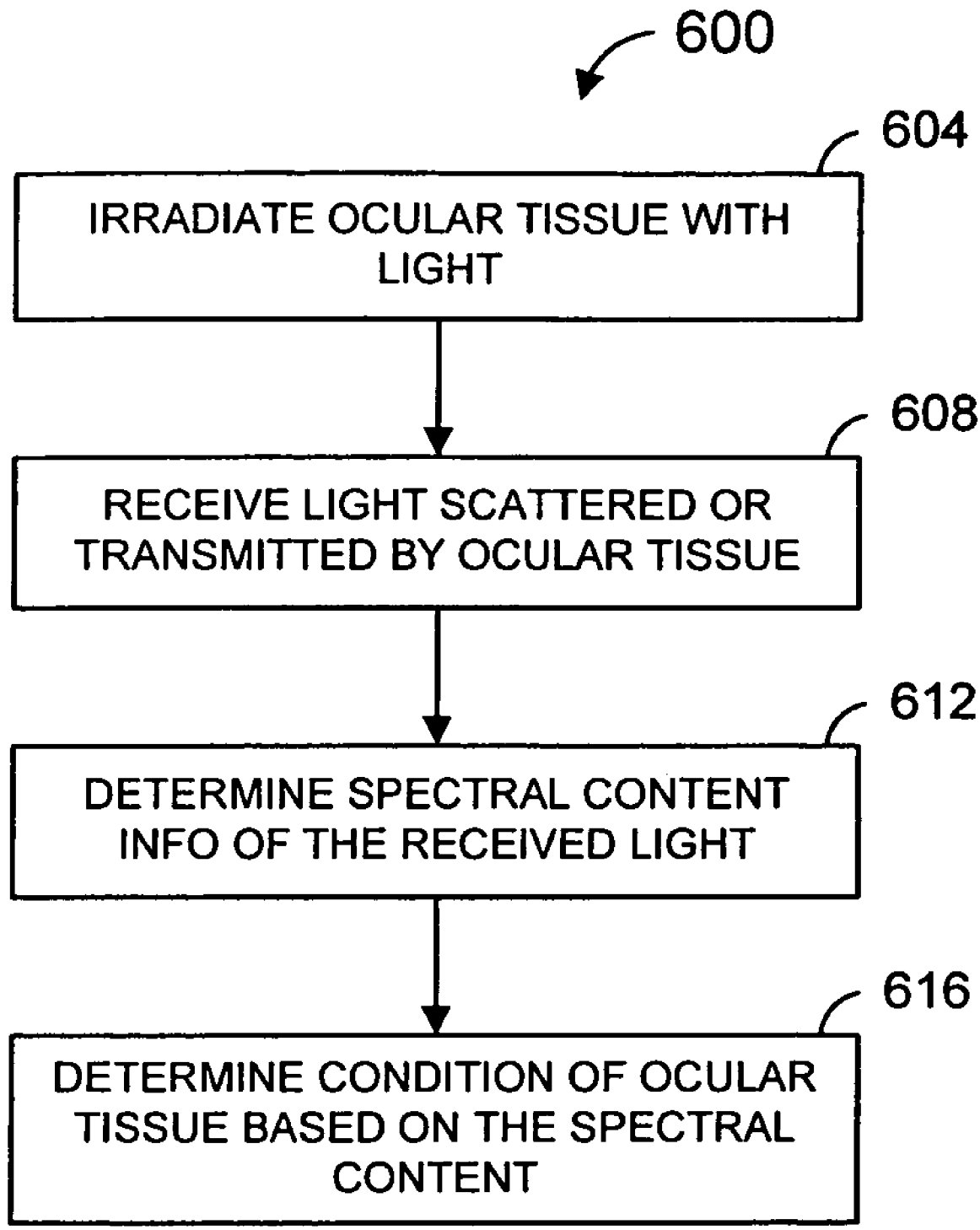
FIG. 13 is a flow diagram of one embodiment of a method for determining an ocular tissue condition.

FIG. 13 is a flow diagram of an example method for determining a condition related to ocular tissue of a patient. The method 600 may be implemented by an apparatus such as the apparatus 100 of FIG. 1, and will be described with reference to FIG. 1. At a block 604, a portion of ocular tissue of a patient is irradiated with light. For example, the optical probe 116 may be used to irradiate the ocular tissue with light generated by the light source 104. In one embodiment, the ocular tissue may be irradiated non-invasively.

At a block 608, light scattered, reflected, or transmitted by the ocular tissue may be collected. For example, the optical probe 116 may collect light scattered by the ocular tissue (Raman spectrometry). As another example, the optical probe 116 may collect light reflected by the ocular tissue ("attenuated total reflection" IR spectrometry). Alternatively, the optical probe 128 may collect light transmitted by the ocular tissue ("line of sight" IR spectrometry). As with the optical probe 116, the optical probe 128 may collect light non-invasively, in one embodiment.

At a block 612, spectral content information associated with the collected light is generated. For example, the light collected by the optical probe 116 or the optical probe 128 may be provided to the spectrum analyzer 132 via the optical processor 140. The spectrum analyzer 132 may then generate spectral content information associated with the light received by the spectrum analyzer 132.

In Raman spectrometry, the spectrum of the collected light scattered from ocular tissue (referred to hereinafter as the "Raman spectrum of the ocular tissue") is indicative of the physico-chemical state of the ocular tissue. The Raman spectrum of the ocular tissue includes bands indicative of various components present in ocular tissue including bands indicative of various components of the collagen matrix of the ocular tissue. The wavelength at which a band is located is indicative of the component, and the height and/or intensity of a band is indicative of the amount of the corresponding component.

Similar to the Raman spectrum of the ocular tissue, in IR spectrometry, the spectrum of the collected light transmitted by the ocular tissue (referred to hereinafter as the "IR spectrum of the ocular tissue") includes bands indicative of components and structure of the ocular tissue. Unlike in Raman spectrometry, however, the bands in the IR spectrum of the ocular tissue are indicative of light absorbed by the ocular tissue, rather than light scattered by the ocular tissue. Nevertheless, the IR spectrum of the ocular tissue is also indicative of the physico-chemical state of the ocular tissue. The Raman spectrum of an ocular tissue and an IR spectrum of the same ocular tissue may provide indications of different components and/or different structure of the ocular tissue.

At a block 616, it is determined whether the patient has an ocular tissue condition based on the spectral content information generated at block 412. For example, the computing device 144 may receive spectral content information from the spectrum analyzer 132. The computing device 144 may then generate an indication, based at least in part on the spectral content information, of whether the patient has an ocular tissue condition. The ocular tissue condition may be, for example, macular degeneration, cataracts, glaucoma, keratitis, scleritis, episcleritis, a genetic disorder, an acquired disorder, etc. Also, the ocular tissue condition may be an increased risk of developing an ocular disease. As further examples, the indication may be of the compatibility of donated ocular tissue, integrity of a cornea after a corneal transplant, an indication of whether cataract surgery is needed, etc.

Figure 6:
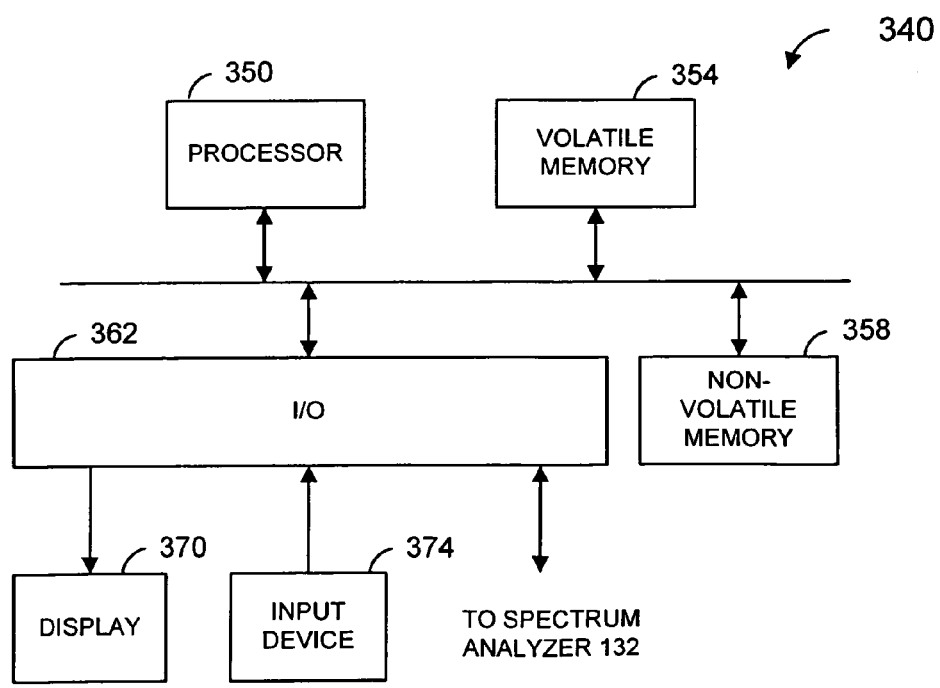
FIG. 6 is a block diagram of a computer that can be used with the apparatus of FIG. 1.

A computing device such as the computing device 340 of FIG. 6 may be used to generate the indication. In some embodiments, the computing device 144 may generate, based on the spectral content information generated at block the 612, an indicator associated with the ocular tissue condition. Such an indicator may be used by a physician to determine whether the patient has an ocular tissue condition, to monitor the progression of an ocular tissue condition, to monitor a response to treatment of an ocular tissue condition, etc.

The determination of the block 616 may be based on additional factors. For example, the determination may be further based on one or more of an age of the patient, a medical history of the patient (e.g., past ocular tissue conditions), a family history of the patient, etc.

Blocks 604, 608, and 612 may optionally be repeated over a period of time (e.g., weeks, months, years) to generate spectral content information that reflects the ocular tissue condition of the patient over the period of time. This spectral content information over the period of time may be used in the determination of block 616.

Experiments

In one experiment, Del 1 (+/−) transgenic mice containing 6 copies of a transgene with a small deletion mutation in the type II collagen gene and that were predisposed to early osteoarthritis were analyzed. The femoral articular cartilage was obtained from Del 1 (+/−) mice at 8 ages (2.5, 3, 5, 7, 9, 10, 13, and 16 months), with age-matched wildtype (wt) controls. The femoral articular cartilage was isolated en bloc and subject to Raman spectroscopy with 785 nm laser excitation and an Olympus BH-2 microscope equipped with a 20×/0.75 NA Zeiss Fluar objective. At each time point, the articular surfaces of three to four transects per femur were examined. Raw spectra were baselined with a polynomial, and curve fitted with GRAMS/AI© software. Bands associated with cartilage matrix proteins were analyzed using the Students t-test. All p values less than 0.05 were considered statistically significant.

Figure 14A:
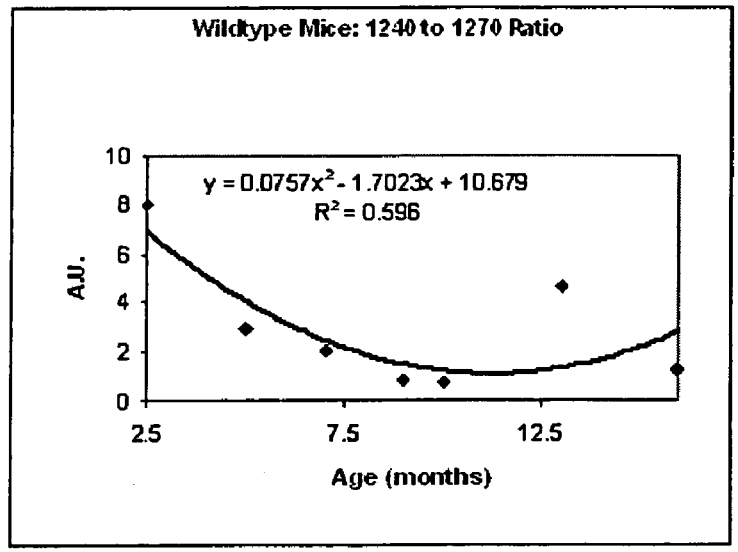
FIG. 14A is a chart showing measured spectral content information associated with cartilage tissue for wildtype mice.
Figure 14B:
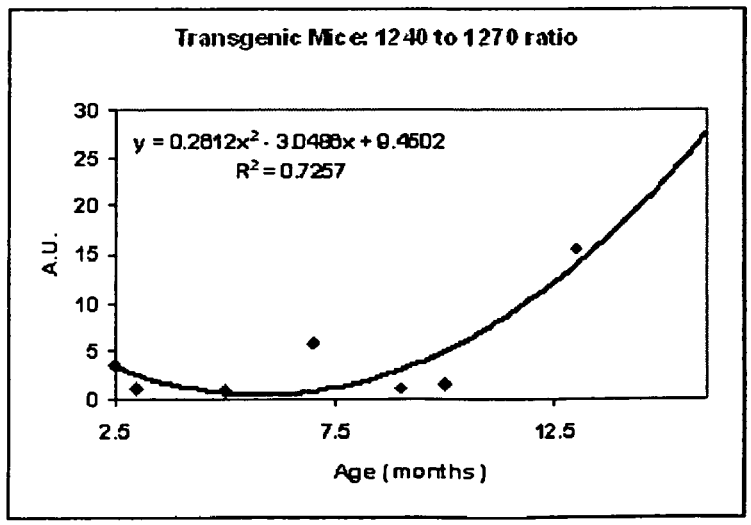
FIG. 14B is a chart showing measured spectral content information associated with cartilage tissue for transgenic mice.

No statistically significant difference was observed between the 2.5 and 3 month old Del1 (+/−) and wt mice. At 5 months of age, however, some differences in the composition and structure of the tissue were detected between the Del 1 (+/−) and wt mice. In general, the Del 1 (+/−) mice had larger carbonate $v_1$:phosphate $v_1$ ($CO_3$:$PO_4$) ratios than wt mice, and this difference increased with age. The higher $CO_3$:$PO_4$ ratio reflects a more carbonated mineral, which is more crystalline and has the potential to compensate for tissue weaknesses. In addition, the Del 1 (+/−) mice exhibited higher 1240 $cm^{-1}$:1270 $cm^{-1}$ band (1240:1270 band) area ratios than their age-matched controls, which indicates a more disordered secondary structure of collagen. The correlation between age and the 1240:1270 ratio was best fit with a second-degree polynomial. FIG. 14A is a graph showing 1240:1270 ratios of wt mice, the second-degree polynomial to which it was fit, and the R value associated with the fit. FIG. 14B is a graph showing 1240:1270 ratios of Del 1 (+/−) mice, the second-degree polynomial to which it was fit, and the $R^2$ value associated with the fit. In both of FIGS. 11A and 11B, the vertical axes are in arbitrary units (A.U.).

Differences between Del 1 (+/−) and wt mice were discerned at as early as 5 months of age. The non-linear relationship between age and the 1240:1270 ratio suggests that at a particular age, the extracellular matrix accumulates changes in the tertiary structure of the collagen fibrils, as is evidenced by the progressive decrease in overall order. This change occurred for the Del 1 (+/−) mice at approximately 6 months of age, and for the wt mice at approximately 11 months of age. It is possible that the 1240:1270 band area ratio indicates the age at which irreversible damage begins to occur within the femoral articular cartilage.

In another experiment, Del 1 (+/−) transgenic mice containing 6 copies of a transgene with a small deletion mutation in the type II collagen gene and that were predisposed to early osteoarthritis were analyzed. Murine femoral articular cartilage was obtained from Del 1 (+/−) mice at 8 ages (2, 2.5, 3, 5, 7, 9, 13, and 16 months), with age-matched wildtype (wt) controls. The Del 1 (+/−) mice had early onset of flattening of femoral condyles, erosion of articular cartilage, sclerosis of subchondral bone, degeneration of the menisci, pyknotic chondrocyte nuclei, with clusters of reactive chondrocytes at the margins of the defects.

Raman spectra were obtained with 785 nm laser excitation. To improve signal-to-noise ratio images were acquired and component spectra were extracted using multivariate analysis allowing the separation of cartilage spectra from mineral spectra. Although there are similarities between the spectra of cartilage and bone matrix, the Raman spectra patterns are distinct because type II collagen is not chemically identical to type I collagen. Additionally, the Raman spectra information includes bands associated with specific proteoglycans in cartilage.

Differences between the Raman spectra of cartilage of Del 1 (+/−) and wt mice were observed. Also, differences in the Raman spectra of cartilage were observed with differences in age. Differences were particularly notable at the 1685 $cm^{-1}$ band, comparing the ages 13 months to 16 months, and comparing the ages 2 months and 7 months. It is believed that differences at the 1685 $cm^{-1}$ band possibly reflect immature crosslinks or ruptured crosslinks in collagen. At each point, the Del 1 (+/−) mice had a higher carbonate/phosphate ratio. This may indicate that Del 1 (+/−) mice cartilage had a more crystalline mineral content. Also, at each point, the Del 1

(+/−) mice had a higher 1240:1270 ratio. This may indicate that Del 1 (+/−) mice cartilage had a more disordered structure of collagen. Further, at each point, the Del 1 (+/−) mice had a lower mineral/matrix ratio, where the mineral/matrix ratio was calculated based on bands associated with carbonate and phosphate (mineral) and a band located at approximately 1446 cm−1 (matrix). This may indicate that Del 1 (+/−) mice cartilage had less mineral per collagen.

In yet another experiment, Del 1 (+/−) transgenic mice were analyzed. For each animal, one or both femurs, with articular cartilage of the knee joints intact, were analyzed from mice at ten ages (2, 2.5, 3, 5, 7, 9, 10, 12, 13, and 16 months), with age-matched wildtype (wt) controls.

Three to 10 transects were taken across the entire femoral articular surface, with a majority of the transects taken along the interior edges of the medial and lateral condyles. Transects taken from the posterior or anterior cruciate ligaments, located between the femoral condyles, were easily distinguishable from cartilage in both white-light images and Raman spectra (data not shown), and were not used in band area calculations. The near-IR excitation laser, 785 nm (Kaiser Optical Systems Invictus), was line-focused through an Olympus BH-2 microscope equipped with a 20×/0.75 NA Zeiss Fluar objective. Incident power on the specimen was approximately 100 mW with a 0.25 neutral density filter. The light was focused to a line approximately 100 micrometers long and 1 micrometer wide. Raman-scattered light was collected through the objective and analyzed by an axial transmissive spectrograph (Kaiser Optical Systems Holospec f/1.8i) operated at 4 $cm^{-1}$ resolution. The scattered light was integrated for 5 minutes on a back-illuminated deep depletion CCD camera (Andor Technology DU 420-BR-DD).

Because line-focusing was used, transects consisting of 254 Raman spectra each, spaced at intervals of 0.5 micrometers along the line, were taken at each sampling area on the femur. From each transect, a normalized mean spectrum was obtained to offset the effect of sample heterogeneity. For each femur, three to ten transects were obtained. Transects were spectra were pre-processed and averaged into a normalized spectrum using MATLAB® software from The MathWorks. The normalized spectra were baselined with a user-defined multi-point baseline, and curve fitted with GRAMS® software from Thermo Electron Corporation. The band envelopes in the baselined spectra were fitted to mixed Gaussian/Lorentzian bands. The constraints for the curve fitting were that all band intensities were non-negative and that the fit yielded an R2 value of 0.99 or greater. The curve fitting procedure generally yeilded bands that were readily identified based on Raman band assignments from previous experiments on bone matrix as summarized in Table 1.

TABLE 1

| Raman Shift ($cm^{-1}$) | Assignment | Component |
|---|---|---|
| 850 | $\nu_{CC}$ hydroxproline | matrix |
| 876 | $\nu_{CC}$ hydroxproline | matrix |
| 945 | disordered apatite | mineral |
| 958 | $\nu_1 PO_4^{3-}$ | mineral |
| 1001 | ring breathing of phenylalanine | matrix |
| 1070 | $\nu_2 CO_3^{2-}$ | mineral |
| 1240 | amide III (disordered) | matrix |
| 1270 | amide III (ordered) | matrix |
| 1450 | $CH_2$ wag | matrix |
| 1667 | amide I | matrix |

Band area ratios were used to measure carbonate:phosphate ratios (carbonate 1070 $cm^{-1}$:phosphate 958 $cm^{-1}$ and 945 $cm^{-1}$), disordered:ordered phosphate (disordered phosphate 945 $cm^{-1}$:ordered phosphate 958 $cm^{-1}$) and cartilage collagen disorder (amide III components, 1240 $cm^{-1}$:1270 $cm^{-1}$, or amide I, 1670 $cm^{-1}$:1685 $cm^{-1}$).

Three to 10 Raman transects were taken on each femur, and a normalized mean spectrum from each transect was used to calculate band areas. All band areas ratios from specimens corresponding to a single age and genotype were grouped to yield a single mean ratio. P-values were determined using Student's T-test (two-tailed with unequal variances).

To elucidate spectral components of cartilage, Raman spectra of solid samples of type I collagen, type II collagen, proteoglycan and chondroitin-6-sulfate were obtained. Spectra from proteoglycan and chondroitin-6-sulfate are not presented because contributions from these two components were not observed in articular cartilage spectra. Previous literature showed that polysaccharide components (chondroitin sulfate, proteoglycan, and keratin sulfate) of non-mineralized cartilage also made an insignificant contribution to the overall Raman spectrum. Raman spectra from types I and II collagen were compared. Spectral features from hydroxyproline, aromatic ring breathing, amide III and amide I are observed (880 $cm^{-1}$, 1001 $cm^{-1}$, 1220-1280 $cm^{-1}$ and 1600-1720 $cm^{-1}$, respectively). An obvious difference in the spectra of solid type I and type II collagen is the location of local peak maxima in the Amide III region. The amide III band corresponding to disordered collagen in type I collagen is located around 1244 $cm^{-1}$, while it is located closer to 1230 $cm^{-1}$ in type II collagen. A comparison of the articular cartilage spectra with these dry reference spectra indicates that major spectral contributions in articular cartilage arose from mineral components and the collagen proteins.

Raw and baselined spectra were compared. The phosphate band at 958 $cm^{-1}$ is strong in the raw spectrum but individual peaks are difficult to identify. Raman spectra of articular cartilage for both wild-type and transgenic mice showed strong mineral signatures at 958 $cm^{-1}$ and 1070 $cm^{-1}$ in addition peaks attributed to type II collagen. Raman bands corresponding to phosphate and carbonate species (958 $cm^{-1}$ and 1070 $cm^{-1}$ respectively) were readily observed and the mean band positions for bands in the amide III region represented type II collagen. Given a variable cartilage depth, the weak Raman scatter of polysaccharide components, and a lower concentration of collagen in the surface layers, this observation was expected. It is believed that a mean normalized spectrum representative of the Raman transect minimized the effects of cartilage depth and sample heterogeneity on band areas.

Raman spectroscopic values for Del1 (+/−) and wt mice are listed in Table 2. Raman spectroscopic analysis revealed no significant spectroscopic difference between the age-matched 2.5 and 3 month old wt and Del1 (+/−) mice. However, by age 6 months, differences in the composition and structure of the tissue between the wt and transgenic mice were identified and these trends continued as the mice aged. With respect to the mineral and matrix components of the Raman spectrum, these data suggest a mechanism of early and rapid type II collagen deterioration in the Del1 (+/−) mice, followed by a biochemical change in the mineral.

TABLE 2

| Specimen Age and Transgenic status | $CO_3:PO_4$ ratio | Amide III ratio | Disordered:Ordered Phosphate ratio |
|---|---|---|---|
| 2 months wt | 0.05 (n = 2) | 1.04 (n = 2) | 0.28 (n = 2) |
| 2 months tg | 0.09 (n = 2) | 0.84 (n = 2) | 0.25 (n = 2) |
| 2.5 months wt | 0.16 ± 0.06 | 7.9 ± 6.8 | 0.33 ± 0.15 |

TABLE 2-continued

| Specimen Age and Transgenic status | $CO_3:PO_4$ ratio | Amide III ratio | Disordered:Ordered Phosphate ratio |
|---|---|---|---|
| 2.5 months tg | 0.14 ± 0.04 | 3.6 ± 1.6 | 0.25 ± 0.15 |
| 3 months wt | 0.10 ± 0.03 | 1.18 ± 0.47 | 0.11 ± 0.05[++] |
| 3 months tg | 0.09 ± 0.02 | 0.75 ± 0.22 | 0.36 ± 0.14[++] |
| 5 months wt | 0.08 ± 0.009[+] | 1.01 ± 0.25 | 0.48 ± 0.12 |
| 5 months tg | 0.1 ± 0.01[+] | 1.03 ± 0.21 | 0.33 ± 0.09[+] |
| 7 months wt | 0.13 ± 0.01[+] | 1.99 ± 0.91[+] | 0.42 ± 0.10 |
| 7 months tg | 0.17 ± 0.02[+] | 5.89 ± 2.23[+] | 0.46 ± 0.07 |
| 9 months wt | 0.07 ± 0.008[+] | 0.81 ± 0.21[+] | 0.37 ± 0.04 |
| 9 months tg | 0.09 ± 0.01[+] | 1.15 ± 0.15[+] | 0.32 ± 0.07 |
| 10 months wt | 0.08 ± 0.02 | 0.71 ± 0.19[+] | 0.17 ± 0.11[++] |
| 10 months tg | 0.07 ± 0.02 | 1.25 ± 0.48[+] | 0.40 ± 0.13[++] |
| 12 months wt | 0.15 ± 0.02 | 0.81 ± 0.21 | 0.33 ± 0.03 |
| 12 months tg | 0.15 ± 0.02 | 0.69 ± 0.15 | 0.31 ± 0.04 |
| 13 months wt | 0.13 ± 0.01[++] | 4.99 ± 1.43[++] | 0.32 ± 0.05 |
| 13 months tg | 0.17 ± 0.008[++] | 1.88 ± 0.60[++] | 0.36 ± 0.05 |
| 16 months wt | 0.07 ± 0.03[+] | 1.25 ± 0.57[+] | 0.38 ± 0.11 |
| 16 months tg | 0.17 ± 0.06[+] | 2.51 ± 0.57[+] | 0.32 ± 0.08 |
| 20 months wt | 0.065 ± 0.14 | 1.22 ± 0.17 | 0.39 ± 0.08 |

With regard to the data in Table 2, mean band area ratios are presented for the wt and Del1 (+/−) mice. The number of transects used in calculating the mean ranged from 2-20, depending on the age and type of mouse. Raman spectra band area ratios are presented as means from all of the specimens per transgenic status and age. The +/− value is the 95% confidence interval, p-values are denoted: [+]$p<0.05$, [++]$p<0.01$. The carbonate: phosphate ratio is the ratio of band areas corresponding to the 1070 $cm^{-1}$ band area divided by the sum of the 958 $cm^{-1}$ and 945 $cm^{-1}$ band areas. The amide III ratio is the ratio of band areas in the amide III envelope corresponding to disordered collagen (1240 $cm^{-1}$) to ordered collagen (1270 $cm^{-1}$). The disordered: ordered phosphate ratio is the ratio of band areas corresponding to disordered apatite (945 $cm^{-1}$) to normal apatite (958 $cm^{-1}$).

Within the Amide III envelope (1220-1280 $cm^{-1}$), the 1240 $cm^{-1}$ band corresponds to a disordered secondary structure of collagen and the 1270 $cm^{-1}$ band corresponds to an ordered secondary structure. The ratio of these two bands may be used to gauge the degree of disorder in collagen's secondary structure. In addition to matrix information, Raman spectra yielded information from peaks that are ascribed to apatite phosphate and carbonate moieties. The carbonate ($CO_3$): phosphate ($PO_4$) band area ratio, 1070 $cm^{-1}$:(958 $cm^{-1}$+945 $cm^{-1}$), may be an indication of the quality of the mineral, since as carbonation of the apatite increases, the mineral crystals become larger. The disordered:ordered phosphate ratio, 945 $cm^{-1}$:958 $cm^{-1}$, may be used to gauge the relative order of the phosphate within the apatite.

Time-based trends in both the mineral and matrix components were analyzed. Data outliers in the 1240 $cm^{-1}$:1270 $cm^{-1}$ ratio were seen at 2.5 months, 7 months (both Del1 (+/−) and wt), and 13 months (wt), and an outlier in the 958 $cm^{-1}$: 945 $cm^{-1}$ ratio was seen at 10 months (wt). These outliers probably result from a low signal-to-noise ratio that affected band area calculations.

A Mankin score, as modified by Turner, et al, was used to evaluate histopathologic changes of OA on the femoral articular cartilage of Del 1 (+/−) and wt mice. In contrast to other studies using the Del1 model, the scores did not consistently increase as a function of age. We observed two significant differences in the Mankin scores: an increase between the 5 and 12 month old wild-type mice (p=0.045) and a decrease in Mankin score between the 2 and 3 month old Del1 (+/−) mice (p=0.020). Mankin scores were not consistent between observers at any of the time points.

The matrix of articular cartilage is comprised of a network of collagen fibers and entrapped proteoglycans. The collagen fibers consist of types II, IX, and XI collagens, but is predominately type II collagen, a homotrimer of three identical α1 (II)-chains. In adults, type II collagen is found mainly in hyaline articular cartilage and in the nucleus propulsus of intervertebral discs, and it is transiently expressed in other areas during embryonic development.

In humans, mutations in Col2a1 have been linked to familial osteoarthritis, as well as mild chondrodysplasia, Stickler and Wagner syndromes, and more lethal syndromes such as type II achondrogenesis (Langer-Saldino syndrome). Similarly, the Del1 (+/−) transgenic mouse develops a progressive articular degeneration phenotype. Studies have shown an increased expression of cartilage oligomeric matrix protein in the Del1 (+/−) articular cartilage, particularly along the tidemark, at the border of calcified and uncalcified cartilage. This increase parallels cartilage degeneration. The chondrocytes at early degenerative lesions of Del1 (+/−) articular cartilage are rich in Sox9, an indicator of chondrocyte activation. The Sox9 staining co-localizes with type IIa procollagen, likely reflecting an attempt at repair. Matrix metalloproteinase-13 mRNA and its inhibitor TIMP-1 are also expressed during early cartilage degeneration in this OA model, and are localized in the synovial tissue, deep calcified cartilage, and subchondral bone. These may be involved in tissue remodeling in response to cartilage damage.

Mankin scoring is a frequently used system for scoring cartilage degradation in animal models of osteoarthritis (Hausser, Osteoarthritis and Cartilage 12: 870-877. 2004; Chu, American Journal of Sports Medicine 32: 699-709, 2004; Lahm, Acta Orthop Scand 75: 762-767, 2004; Tibesku, Arthritis & Rheuimatism 52: 810-817, 2005). Within the Mankin system, sub-scores are given for surface integrity, hyper- and hypo-cellularity, and matrix quality using hematoxylin/eosin and Safranin-O staining. The final score ranges from 0 (no osteoarthritis) to 20 (severe osteoarthritis). Murine models of OA are more often graded with a less descriptive 0 through 3 score (de Hooge, Osteoarthritis and Cartilage, 13: 66-73, 2005; Zemmyo Arthritis & Rheumatism 48: 2873-2880, 2003), a 0 through 4 score (Helminen. Journal of Clinical Investigation 92: 582-595, 1993; Saamanen, Osteoarthritis and Cartilage, 8: 248-257, 2000) a 0 through 5 score (Lapvetelainen, Annals of Rheum Dis 61: 810-817, 2002), or a 0 through 6 score (Mistry, Osteoalthritis and Cartilage 12: 131-141, 2004; Glasson, Arthritis & Rheumatism 50: 2547-2558, 2004). A review of the literature reveals one other murine study using a modified Mankin scoring system (Xu, Arthritis & Rheumatism 48: 2509-2518, 2003).

The modified Mankin score has been validated as an adequate measure of histological damage in at least one animal model of OA. The authors of this validation study examined rabbit articular cartilage, comparing wild-type to experimental OA (either medial meniscectomy or plaster immobilization extension), with each sample being evaluated by two blinded observers. They found that most scores were less than 6, with reasonable intra-observer agreement (standard deviation varying between 1.5 and 2.6 points). Other researchers, however, have questioned the validity of this scoring system and have identified inherent problems associated with both inter- and intra-observer variation. In the present experiment, significant inter-observer variation were observed and the mean score did not consistently increase as a function of age. Statistical analyses showed no significant differences between Del1 (+/−) and wild-types in total modified Mankin scores at ages 2, 3, 10, or 13 months of age (FIG. 7c). In contrast to the high degree of variability using conventional histology, the spectra obtained using Raman spectra were consistent from animal to animal. Raman spectra were normalized to minimize sample heterogeneity. Thus, any changes observed in band area ratios was more likely due to biochemical changes in the mineral or matrix than to decreased scatter from the collagen matrix.

Previous studies have shown that compared to wt mice, Del1 (+/−) mice have collagen with greater fiber disorder. Raman spectra results of the present experiment are consistent with these prior reports, as seen by an increased 1240 $cm^{-1}$:1270 $cm^{-1}$ band area ratio for the age-matched Del1 (+/−) mice. This increased ratio indicates a more disordered secondary structure for collagen, suggesting the Del1 (+/−) mice had an altered molecular response to the truncated type II collagen fiber. Del1 (+/−) mice showed an increasing 1240 $cm^{-1}$:1270 $cm^{-1}$ ratio starting at approximately 6 months of age. The wt mice maintained a more ordered collagen secondary structure for a longer period of time, with a slight gradual upward trend starting at approximately 12 months of age. The increasing disorder of collagen in the Del1 (+/−) articular cartilage is consistent with the abnormal light microscopy seen in previous studies.

The 1685 $cm^{-1}$:1667 $cm^{-1}$ ratio (ratio of the 2 bands in the amide I envelope) in Del1 (+/−) mice increased at a rate about 1.5 times greater than the wt 1685 $cm^{-1}$:1667 $cm^{-1}$ ratio (data not shown). As observed in bone, and also expected for cartilage, the 1685 $cm^{-1}$:1667 $cm^{-1}$ ratio increases as tissue damage progresses. While the differences in the amide I envelope may be reflective of contributions from both types I and II collagen, these data add weight to the argument that Raman spectra can readily detect increased fragility of collagen crosslinks in Del1 (+/−) mice. Due to the intricate ultrastructure of tissues such as cartilage, it is expected that structural changes in collagen (in this case truncation) will also cause changes in the mineral content of the mineralized layer of cartilage.

Data from the present experiment tend to show that Del1 (+/−) mice have an increased $CO_3$:$PO_4$ ratio when compared to wt mice. A more carbonated mineral is more crystalline and thus has the potential to compensate for other tissue weaknesses or disorder. Other studies of mineralized tissues have shown an increase in $CO_3$:$PO_4$ ratio for osteoarthritic joints. The $CO_3$:$PO_4$ ratio increased with age in the Del1 (+/−) and wt mice, until approximately 7 months of age, and increased again after 10 months for the Del1 (+/−) mice. The elevated carbonate content in the older transgenic mice may be indicative of an increased mineralization to compensate for a degraded collagen matrix or as a chemical response to the decreasing pH of the synovial fluid. Both mechanisms are plausible, as lower pH and increased mineralization of cartilage in OA patients has been reported. It is possible that, in the Del1 (+/−) model, the mineral becomes more carbonated as a response to the inherent instability of matrix composed of truncated type II collagen fibers.

Further analysis of the mineralized species revealed that while there was an increase in carbonated apatite in the Del1 (+/−) mice, there was no significant change in the relative order of the phosphate species. In previous studies, the Raman band at 945 $cm^{-1}$ generally corresponded to a more disordered phosphate species. The ratio of the 945 $cm^{-1}$ to the 958 $cm^{-1}$ bands can be used to further assess the mineralization process. The relative amount of disordered phosphate was observed to plateau at approximately 9 months for both the Del1 (+/−) and wt mice. There was no statistically significant difference (p>0.15) between the wt and Del1 (+/−) mice after 5 months, except at age 10 months. The data for the wt and Del1 (+/−) mice can be fitted into a parabolic shaped curve with an apparent plateau of this ratio after 9 months. Thus, the increased carbonation, as seen in older Del 1 (+/−) mice, may be either a result of the substitution from both the ordered and disordered phosphate mineral species or as an increased carbonate secretion as a chemical response to acidic synovial fluid.

The Del1 transgenic mouse is a model of human OA characterized by altered cartilage matrix structure. It was hypothesized that RS of Del1 transgenic femoral articular cartilage would identify age-dependent patterns that would correlate with histomorphometric changes characteristic of OA. Consistent changes in Del1 (+/−) articular cartilage Raman spectral patterns over time were observed, which were not seen in wt samples. The increasing amide III ratio and the increasing $CO_3$:$PO_4$ ratio distinguish the Del1 (+/−) samples from the wt samples at an early age. Moreover, time-based trends for early collagen deformation and subsequent mineral changes that may be reacting to the disordered collagen were observed.

Previous studies show that the weight difference between Del1 (+/−) and wild-type mice is greater for male than female mice. In the present experiment, due to insufficient numbers of mice, they were not matched for gender. This random gender pairing could have affected the Raman spectra. To address this issue multiple mice at each age were evaluated. The data for male and female mice were graphed separately, and no significant differences were observed. Thus, it appears that the data analysis was not biased by the genders of the mice evaluated.

In still another experiment, Del 1 (+/−) ocular tissue from a wildtype mouse, aged 20 months, and younger mice but of unknown ages (a transgenic mouse and a wildtype mouse) were analyzed. At least seven transects were taken from each eye, although not all transects produced a usable signal either due to fluorescence or sample movement. The transects were preprocessed to remove curvature and spikes, and dark-subtract spectra. The spectra were baselined and peak-fitted using GRAMS/AI spectroscopy software available from Thermo Electron Corporation. Peak areas were recorded if the curve-fit showed an $R^2$ greater than 0.990 and had no negative peaks. The averaged peak areas were from both eyes. A 5×/0.25 NA objective and a 0.3 neutral density filter (laser intensity at objective approximately 105 mW) was used to help keep the entire specimen in focus despite the large radius of curvature of the eye, and to help avoid specimens burning.

Figure 15:
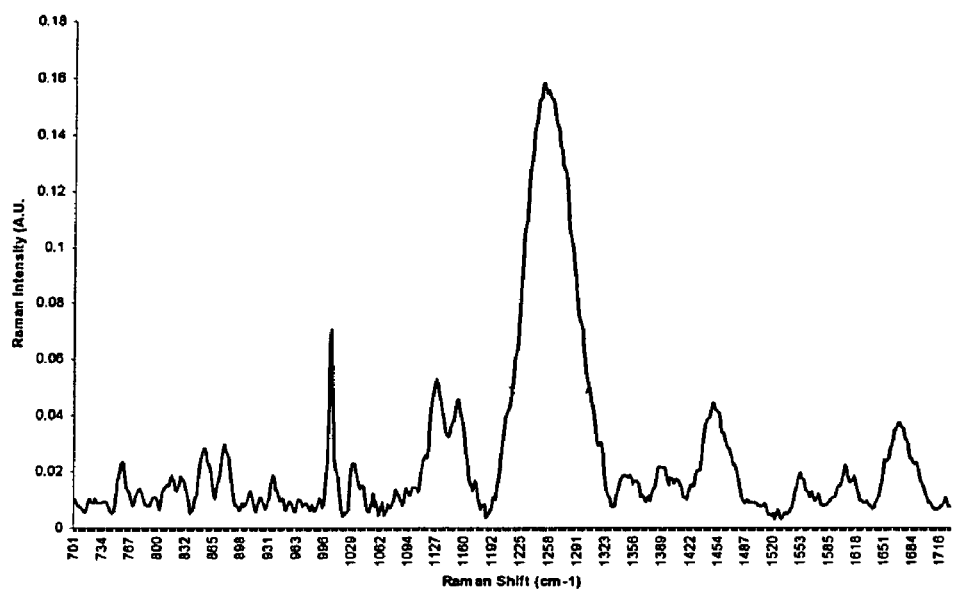
FIG. 15 is a graph of a Raman spectrum of ocular tissue.
Figure 16:
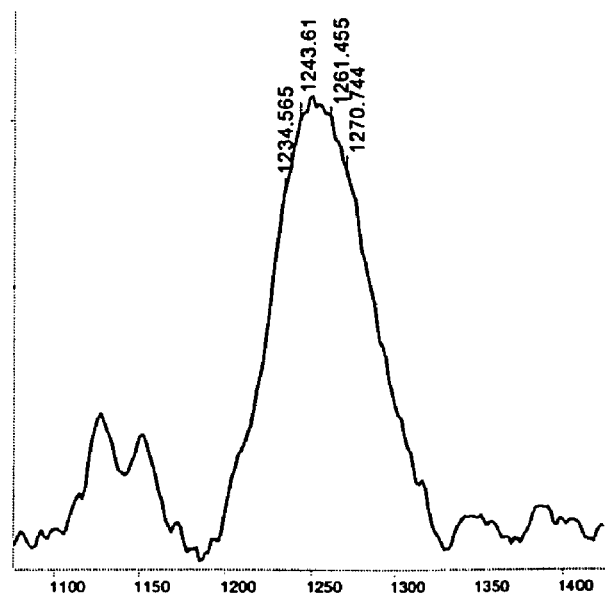
FIG. 16 is a portion of the graph of FIG. 15.

The Del1 mice are well-characterized animal models for early-onset osteoarthritis because they have collagen fibrils truncated by 15 amino acids, the result of a 150 basepair deletion mutation. Expression of this truncated collagen gene is also seen in ocular tissue, and it is postulated that the Del1 mice may also be used to model age-related degeneration in the eye. It was observed that the amide III envelope (1220-1320 $cm^{-1}$) had the most consistent signal. The 1230:1260 band ratios were looked at when comparing transgenic and wildtype. The ratio of 1230:1260 area bands are used to estimate disorder in collagen, with contributions from crosslinking and degree of hydration. A Raman spectrum of the ocular globe is presented in FIG. 15. FIG. 16 is a portion of the Raman spectrum of FIG. 15. Contributions from ocular tissue, amino acids and collagen are distinguishable, and band assignments are provided in Table 3. The amide III envelope in ocular tissue appears wider than the amide III envelope in articular cartilage, likely due to several types of collagen structure in the ocular tissue.

TABLE 3

| Sample ID | 1230:1260 Ratio (Average) | St. Dev. |
|---|---|---|
| Del1 mouse, unknown age | 0.9080 (+/−0.159) | 0.1812 |
| Wildtype mouse, unknown age | 0.5587 (+/−0.136) | 0.2298 |
| Wildtype mouse, 20 months | 0.9857 (+/−0.127) | 0.2143 |

With respect to articular cartilage of mice, an increased 1230:1260 ratio as a function of age was observed in Del1 mice, whereas there was no observable difference in wildtype mice. In the analysis of ocular tissue, there was a statistically significant (p=0.008) discrepancy of ratios between the Del1 and wildtype for the mice of unknown age. As seen in Table 3, the Del1 mouse of unknown age has a higher 1230:1260 ratio, as expected. The 1230:1260 ratio of the 20-month wildtype mouse is comparable but not statistically significant (p=0.4) to that of the Del1 mouse, indicating that collagen deformation caused by the transgene is comparable to months of the normal "wear and tear" as seen in an older wildtype mouse. Upon comparison between the two wildtype mice, there is a significant statistical difference in the values (p<0.01).

A statistically significant difference in the 1230:1260 band ratios when comparing Del1 and wildtype mice was seen. The transgenic mice show increased collagen disorder, as expected, compared to the wildtype mice. Moreover, increased collagen disorder as a function of mouse age was seen.

In yet another experiment, eyes were excised from Del1 (+/−) and wild-type (wt) mice including a 12-14 month transgenic mouse, a 12-14 month wild-type mouse, and a 20 month old wild-type mouse.

An eye mount was constructed and included a disposable tube cap secured onto a microscope slide and filled with pH 7.4 phosphate buffered saline (PBS). A "blank" spectrum of the eye mount filled with PBS (spectrum not shown) confirmed that the spectral features of ocular tissue arose from the eye tissue, with minimal spectral interference from the mount. Minor contributions from the phosphate buffer/polypropylene cap were observed at 1883 $cm^{-1}$ and 1151 $cm^{-1}$ in spectra taken from eye tissue. Both eyes from each specimen were analyzed.

A 5×/0.25 NA objective and a 0.3 neutral density filter (laser intensity at objective ~105 mW) was used to avoid specimen burning and keep the entire specimen in focus, despite the small radius of curvature of the eye. The Raman signal was integrated for 600 seconds on a charged coupled device (CCD) detector to maximize the signal-to-noise ratio (SNR). Specimens were analyzed with no coverslip over the mount. The levels of PBS in the mount were continually monitored and refreshed as needed. The outer edges of the sclera were examined. Raman transects, point spectroscopy at intervals along a line, were taken along these outer sclera edges. Spectra from transects with excessive fluorescence interference or specimen movement were discarded.

Transects were pre-processed using MATLAB® software from The MathWorks to remove curvature and spikes, and to remove the dark signal from the spectra. To minimize the effect of sample inhomogeneity on band areas, a single normalized spectrum (representative of the entire transect) was exported to the GRAMS® software after the initial processing. The spectra were baselined and the amide III envelope was peak-fitted using GRAMS/AI software. Peak areas were recorded if the best-fit curve showed an $R^2$ greater than 0.990 and had no negative peaks. The peak areas for both eyes were grouped together to form a single average value for each specimen.

Depending on the specimen, spectra from five to twelve Raman transects were used to calculate an average band area ratio. All band areas ratios from specimens corresponding to a single age and transgenic status were grouped to yield a single averaged ratio. Student's T-tests (two-tailed with unequal variances) were used to compare band ratios between the transgenic and wild-type (wt) mice and between ageing wt mice. P-values below 0.05 are denoted in Table 4 by +, p-values below 0.01 are denoted in Table 4 by ++.

TABLE 4

| Specimen transgenic status and age | 1235 $cm^{-1}$:1265 $cm^{-1}$ Ratio | Std. Dev. |
|---|---|---|
| Wild-type, age 12–14 months N = 12 | 0.5587 (±0.136) | 0.2298 |
| Wild-type, age 20 months N = 11 | 0.9857 (±0.127) | 0.2143 |
| Del1 (+/−), age 12–14 months N = 5 | 0.9080 (±0.159) | 0.1812 |

Figure 17:
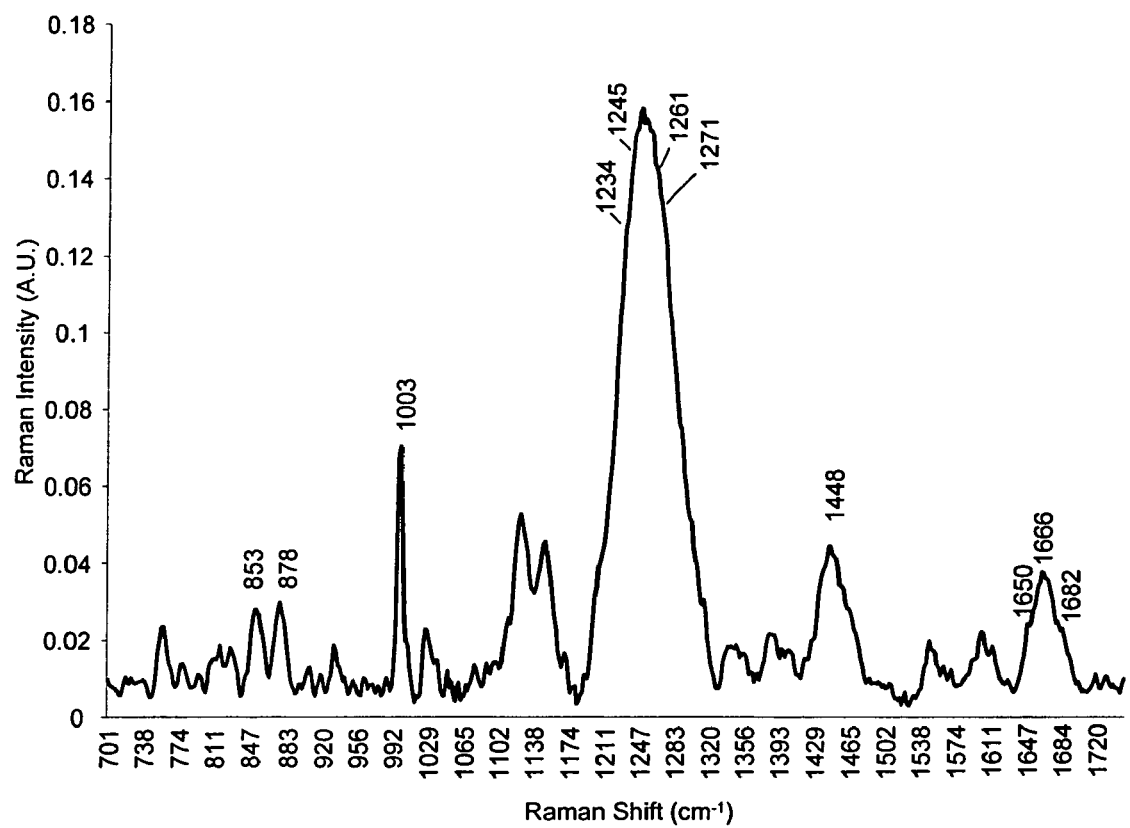
FIG. 17 is another graph of a Raman spectrum of ocular tissue.
Figure 18:
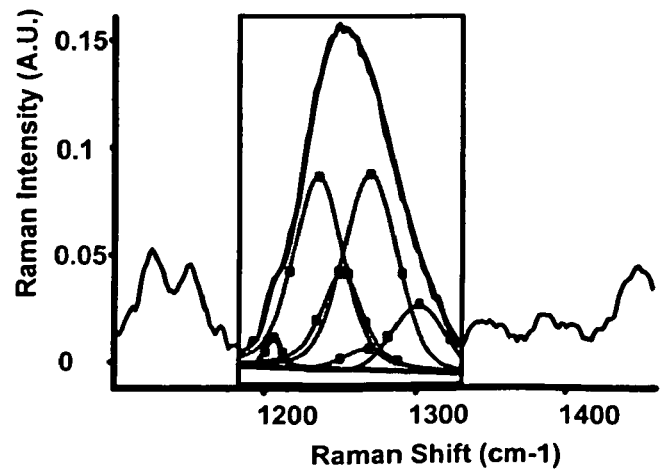
FIG. 18 is a graph showing an example of peak fitting in a region of the graph of FIG. 17.
Figure 19:
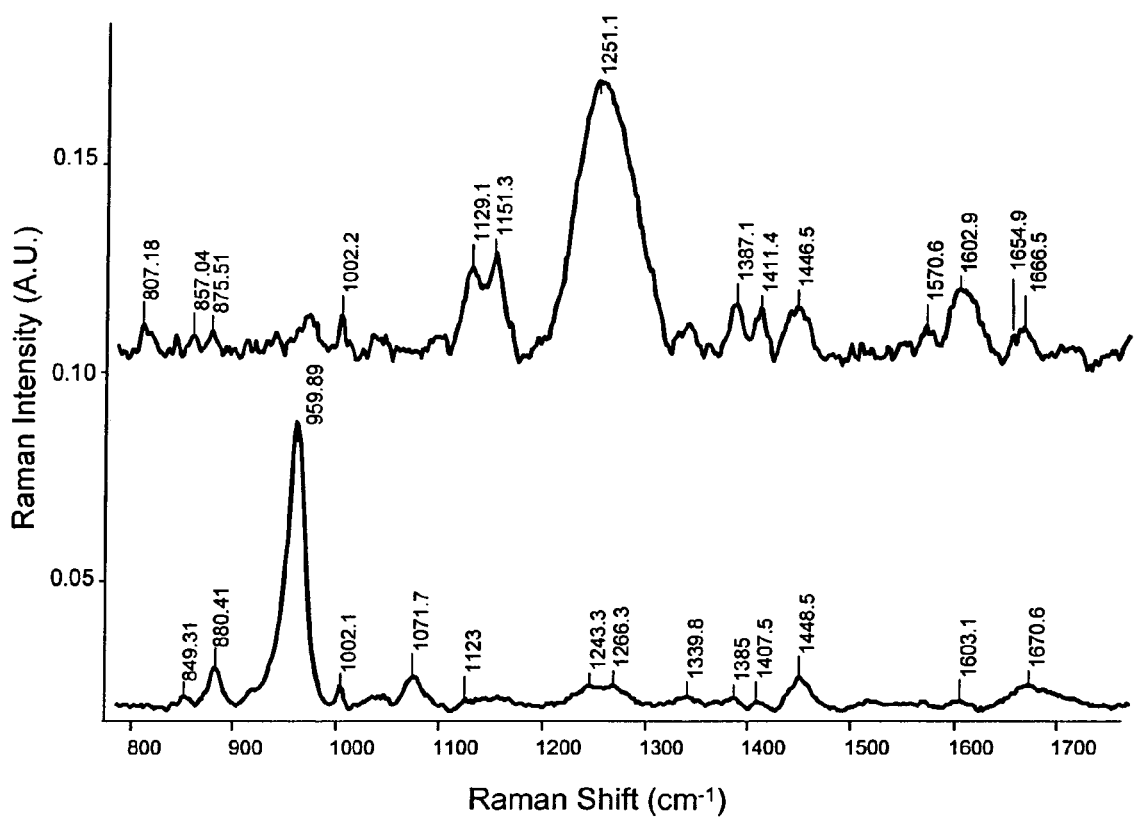
FIG. 19 is a Raman spectrum of articular cartilage (upper plot) and a Raman spectrum of eye tissue (lower plot) taken from a single mouse specimen.

A Raman spectrum of eye tissue is presented in FIG. 17, and an example of peak fitting in the amide III region of FIG. 17 is presented in FIG. 18. An amide III envelope analysis was used to estimate disorder in collagen. The maximum at a lower Raman shift (range: 1230-1240 $cm^{-1}$) may be associated with disordered collagen fiber, and the maxima at a higher Raman shift (range: 1260 1270 $cm^{-1}$) may be associated with ordered collagen. For eye tissue, the maxima were 1235 $cm^{-1}$ and 1265 $cm^{-1}$ and an amide III ratio was determined as the ratio of the 1235 $cm^{-1}$ and 1265 $cm^{-1}$ band areas. Increases in the amide III ratio may indicate an increase in the disorder of the collagen fiber. Amide III band ratios may also be used to gauge collagen disorder in comparisons in articular cartilage from Del1 (+/−) transgenic and wild-type mice. Spectral contributions from ocular tissue, amino acids and collagen are distinguishable in FIG. 17. Band assignments are provided in Table 5 and are based on previous assignments of ocular tissue from the literature. Bands at 1235, 1240, 1265 and 1270 $cm^{-1}$ are visible in the amide III envelope, likely due to several types of collagen structure in the ocular tissue. FIG. 19 illustrates the Raman spectra of articular cartilage (upper plot) and Raman spectra of eye tissue (lower plot) taken from the same specimen. As can be seen in FIG. 19, local maxima in the amide III envelope are less defined in ocular tissue than in articular cartilage, as seen in FIG. 19. Contributions from phosphate and carbonate mineral components at 959 $cm^{-1}$ and 1070 $cm^{-1}$, as observed in Raman spectra of articular cartilage, are not observed in eye tissue.

TABLE 5

| Raman Shift ($cm^{-1}$) | Band Assignment | Component |
|---|---|---|
| 642 | Aromatic | Collagen Tyrosine |
| 757 | Aromatic | Tryptophan |
| 877, 853, 827 | Aromatic | Tryptophan |
| 1003 | Aromatic ring breathing | Phenylalanine |
| 1220–1280 | Amide III envelope | Collagen |
| 1450 | C—H scissor | Ocular Tissue |
| 1650 | O—H bend | Water/Ocular Tissue |
| 1667 | Amide I | Collagen |
| 1685 | Amide I | Collagen |

Raman spectra of eye tissue from the Del1 (+/−) mouse showed a deformed collagen fiber that was also observed in the aged wild-type mouse. In the analysis of ocular tissue, there is a statistically significant (p=0.008) difference of ratios between the 12-14 month transgenic and wild-type specimens. As seen in Table 4, the transgenic mouse has a higher $1235\,cm^{-1}$:$1265\,cm^{-1}$ ratio, as expected. The amide III ratio of the 20 month wild-type mouse is comparable to that of a transgenic mouse, indicating that collagen deformation caused by the transgene may be comparable to 20 months of the normal ageing as seen in the older wild-type mouse. The wild-type mice also show a significant statistical difference in the measured ratios (p<0.01), which may indicate that collagen deformation in older wild-type mice occurs due to the natural effect of ageing and the low turnover rate of ocular collagen. An increase in collagen deformation as a function of age in wild-type mice is expected and a slight increase in the amide III ratio was also observed in Raman analysis of femurs from ageing wild type mice.

In addition to a higher band area ratio, the average peak position in the amide III envelope may provide another marker of collagen damage in the transgenic and 20 month specimens. Raman spectroscopy of proteins has shown that changes in the secondary structure, due to environmental, mechanical, or chemical stresses, will give rise to changes in band position, band area or both. Unlike articular cartilage, eye collagen is not subject to damage from mechanical loads and the observed shifts in band position are plausibly the result of chemical modifications, such as an altered cross-link content, that may affect the elasticity of the collagen fiber. The shift to higher wavenumbers in the amide III region may be another indication of collagen fiber deformation that is due to either the truncated collagen or long-term normal use, depending on the transgenic status of the mouse. There is a shift to a higher wavenumber for the $1235\,cm^{-1}$ peak for the 20 month wild-type and transgenic mouse. Spectra from the 12-14 month transgenic and 20 month wild-type mouse have an average peak position of $1234\,cm^{-1}$ (±1.7) and $1236\,cm^{-1}$ (±2.0) respectively, while spectra from the 12-14 month wild-type mouse have an average peak position of $1231\,cm^{-1}$ (±1.4). The difference in band position seen in the 12-14 month wild type mouse is statistically different (p<0.05) from both the 12-14 month transgenic and 20 month wild type mice.

There is a statistically significant difference in the amide III band ratios between the 12-14 month transgenic and wild-type mice. The transgenic mouse showed a higher collagen disorder, as expected, compared to its age-matched wild-type littermate. Moreover, the increased collagen disorder in the 20 month wild-type mouse may indicate that Raman can also identify changes to collagen that are a result of normal ageing. Truncation of the collagen fiber caused by the transgene or loss of collagen fiber elasticity from normal ageing causes deformation that is observed in both the amide III band area ratio and band position associated with disordered collagen in the amide III region. Raman spectroscopy yields useful markers to identify increased collagen disorder in both transgenic mice and older wild type mice. Raman bands in the amide III envelope can be used as markers for collagen fiber disorders in eye tissue. Because it is non invasively accessible, eye tissue may serve as a good site for study of collagen damage due to genetic defects or the natural ageing process.

At least portions of the techniques described above, including the blocks described with reference to FIGS. 2-4 and 7-13, may be implemented using software comprising computer program instructions. Such computer program instructions may control the operation of a computing device such as a desktop computer, a laptop computer, a tablet computer, a workstation, a server, a mainframe, etc. The computing device may have a memory in which the computer program instructions may be stored. The computer program instructions may be written in any high level language such as C, C++, C#, Java or the like or any low-level assembly or machine language. By storing computer program instructions in a memory of the computing device, the computing device is physically and/or structurally configured in accordance with the computer program instructions.

While many methods and systems have been described herein as being implementable in software, they may be implemented in hardware, firmware, etc., and may be implemented by a variety of computing systems and devices. Thus, at least some method blocks and system blocks described herein may be implemented in a standard multi-purpose central processing unit (CPU), a special purpose CPU, or on specifically designed hardware or firmware such as an application-specific integrated circuit (ASIC) or other hard-wired device as desired. When implemented in software, the software routine may be stored in any computer readable memory such as on a magnetic disk, a laser disk (such as a compact disk (CD), a digital versatile disk (DVD)), a flash memory, a memory card, a memory stick, etc., or other storage medium, in a RAM or ROM of a computer or processor, in any database, etc. Likewise, this software may be delivered via any known or desired delivery method including, for example, on a computer readable memory or other transportable computer storage mechanism or over a communication channel such as a telephone line, the internet, etc. (which are viewed as being the same as or interchangeable with providing such software via a transportable storage medium).

While the invention is susceptible to various modifications and alternative constructions, certain illustrative embodiments thereof have been shown in the drawings and are described in detail herein. It should be understood, however, that there is no intention to limit the disclosure to the specific forms disclosed, but on the contrary, the intention is to cover all modifications, alternative constructions and equivalents falling within the spirit and scope of the disclosure as defined by the appended claims.

What is claimed is:

1. A method for evaluating a connective tissue condition of a patient, the method comprising:
    irradiating a portion of tissue of the patient using a light source, the tissue at a first location of the body of the patient, wherein the portion of tissue from tissue at the first location comprises at least one of ocular tissue, nasal cartilage tissue, or ear cartilage tissue;
    receiving light from the portion of the tissue;
    determining spectral content information associated with the received light; and
    generating, based at least on the spectral content information, an indicator of a connective tissue condition associated with connective tissue at a second location of the body of the patient, the second location remote from the first location;
    wherein the connective tissue at the second location comprises cartilage from at least one of a joint of the hand, a joint of the foot, a knee joint, a hip joint, a back joint, or a neck joint; and
    wherein generating the indicator of the connective tissue condition associated with connective tissue at the second location comprises measuring, in the spectral content information, parameters indicative of the connective tissue condition associated with connective tissue at the second location.

2. A method as defined in claim 1, wherein generating the indicator of the connective tissue condition comprises generating an indicator of a bone tissue condition.

3. A method as defined in claim 1, wherein generating the indicator of the connective tissue condition comprises generating an indicator of a cartilage tissue condition.

4. A method as defined in claim 1, wherein irradiating the portion of tissue of the patient using the light source comprises irradiating the portion of tissue of the patient using a substantially monochromatic light source that produces light having a wavelength substantially between 700 nanometers and 1100 nanometers.

5. A method as defined in claim 4, wherein irradiating the portion of tissue of the patient using the substantially monochromatic light source comprises at least one of:
    irradiating the portion of tissue of the patient using a substantially monochromatic light source that produces light having a wavelength of substantially 785 nanometers; or
    irradiating the portion of tissue of the patient using a substantially monochromatic light source that produces light having a wavelength of substantially 830 nanometers.

6. A method as defined in claim 1, wherein irradiating the portion of tissue of the patient comprises at least one of irradiating the portion of tissue in vivo, irradiating the portion of the tissue through the skin of the patient, irradiating the portion of the tissue via an incision in the patient, and irradiating a biopsy of tissue removed from the patient.

7. A method as defined in claim 1, wherein receiving light from the portion of the tissue comprises at least one of receiving light scattered from the portion of the tissue, receiving light transmitted through the portion of the tissue, and receiving light reflected by the portion of the tissue.

8. A method as defined in claim 1, wherein determining spectral content information comprises at least one of determining Raman spectra and determining infrared spectra.

9. A method as defined in claim 1, wherein generating the indicator of the connective tissue condition comprises generating an indicator associated with at least one of osteoarthritis, rheumatoid arthritis, chondromalacia, polychondritis, relapsing polychondritis, a genetic disorder, and an acquired disorder.

10. A method as defined in claim 1, wherein the spectral content information includes a plurality of bands corresponding to received light at one or more wavelengths;
    wherein generating the indicator of the connective tissue condition comprises determining at least one intensity of at least one band.

11. A method as defined in claim 10, wherein determining the at least one intensity of the at least one band comprises at least one of:
    fitting a curve to at least one band;
    calculating an area of at least one band; or
    calculating a height of at least one band.

12. A method as defined in claim 10, wherein generating the indicator of the connective tissue condition comprises:
    determining a first intensity of at least a first band;
    determining a second intensity of at least a second band; and
    determining a first ratio of the first intensity and the second intensity.

13. A method as defined in claim 12, wherein generating the indicator of the connective tissue condition further comprises generating the indicator based at least in part on the first ratio.

14. A method as defined in claim 12, wherein the first band comprises at least one of:
    a carbonate band;
    a phosphate band;
    a band at circa 1230 $cm^{-1}$;
    a band at circa 1240 $cm^{-1}$;
    a band at circa 1260 $cm^{-1}$; or
    a band at circa 1270 $cm^{-1}$;
    and wherein the second band comprises at least one of:
    a carbonate band;
    a phosphate band;
    a band at circa 1230 $cm^{-1}$;
    a band at circa 1240 $cm^{-1}$;
    a band at circa 1260 $cm^{-1}$; or
    a band at circa 1270 $cm^{-1}$.

15. A method as defined in claim 1, further comprising determining whether the patient has the connective tissue condition based on the indicator of whether the patient has the connective tissue condition and on at least one of an age of the patient, height of the patient, a weight of the patient, prior weight history of the patient, a blood test, a synovial fluid test, a bone mineral density of the patient, an X-ray, prior medical history of the patient, and a family history of the patient.

16. A method as defined in claim 1, wherein the connective tissue condition is osteoarthritis.

17. A method as defined in claim 16, wherein the portion of tissue from tissue at the first location comprises ocular tissue.

18. An apparatus for evaluating a connective tissue condition of a patient, comprising:
    a light source;
    a light receiver to receive light from a portion of tissue of a patient irradiated by the light source, the tissue from a first location of a body of the patient, wherein the portion of tissue from tissue at the first location comprises at least one of ocular tissue, nasal cartilage tissue, or ear cartilage tissue;
    a spectrum analyzer optically coupled to receive light received by the light receiver, the spectrum analyzer configured to generate spectral content information associated with the received light; and
    a computing device communicatively coupled to the spectrum analyzer, the computing device configured to generate diagnostic information indicative of a connective tissue condition based at least in part on the spectral content information, the connective tissue condition associated with connective tissue at a second location of the body of the patient, the second location remote from the first location;
    wherein the connective tissue at the second location comprises cartilage from at least one of a joint of the hand, a joint of the foot, a knee joint, a hip joint, a back joint, or a neck joint; and
    wherein the computing device is configured to measure, in the spectral content information, parameters indicative of the connective tissue condition associated with connective tissue at the second location.

19. An apparatus as defined in claim 18, wherein the computing device is configured to generate diagnostic information indicative of a cartilage tissue condition.

20. An apparatus as defined in claim 18, wherein the computing device is configured to generate diagnostic information indicative of a bone tissue condition.

21. An apparatus as defined in claim 18, wherein the light source comprises a substantially monochromatic light source.

22. An apparatus as defined in claim 21, wherein the light source produces light having a wavelength substantially between 700 nanometers and 1100 nanometers.

23. An apparatus as defined in claim 18, wherein the light source comprises an infrared light source.

24. An apparatus as defined in claim 18, wherein the light receiver comprises at least one of a microscope, an optical probe, or a lens coupled to a needle.

25. An apparatus as defined in claim 18, wherein the computing device comprises at least one of a digital circuit, an analog circuit, a mixed analog and digital circuit, or a processor coupled to a memory.

26. An apparatus as defined in claim 18, wherein the connective tissue condition comprises at least one of osteoarthritis, rheumatoid arthritis, chondromalacia, polychondritis, relapsing polychondritis, a genetic disorder, and an acquired disorder.

27. An apparatus as defined in claim 26, wherein the spectral content information includes a plurality of bands corresponding to received light at one or more wavelengths;
    wherein the computing device is configured to determine at least one intensity of at least one band.

28. An apparatus as defined in claim 27, wherein the computing device is configured to, at least one of:
    fit a curve to the at least one band;
    determine an area of at least one band; or
    determine a height of at least one band.

29. An apparatus as defined in claim 18, wherein the computing device is configured to determine a first intensity of at least a first band;
    wherein the computing device is configured to determine a second intensity of at least a second band; and
    wherein the computing device is configured to determine a first ratio of the first intensity and the second intensity.

30. An apparatus as defined in claim 18, wherein the computing device is configured to generate the diagnostic information indicative of the connective tissue condition further based on at least one of age of the patient, a height of the patient, a weight of the patient, a prior weight of the patient, blood test data, synovial fluid test data, a bone mineral density of the patient, data associated with an X-ray, prior medical history data, and family history data.

31. An apparatus as defined in claim 18, wherein the connective tissue condition is osteoarthritis.

32. An apparatus as defined in claim 31, wherein the portion of tissue from tissue at the first location comprises ocular tissue.

* * * * *